United States Patent [19]
Suto et al.

[11] Patent Number: 5,932,618
[45] Date of Patent: Aug. 3, 1999

[54] ANTI-VIRAL AGENTS AND METHODS RELATING TO THE USE THEREOF

[75] Inventors: Carla M. Suto; Jun Wu; Leah M. Gayo, all of San Diego, Calif.

[73] Assignee: Signal Pharmaceuticals, Inc., San Diego, Calif.

[21] Appl. No.: 08/740,711

[22] Filed: Nov. 4, 1996

[51] Int. Cl.$^6$ .................................................. A61K 31/19
[52] U.S. Cl. .......................... 514/568; 514/567; 514/532; 514/535; 514/619; 514/622
[58] Field of Search ..................... 514/567, 568, 514/532, 535, 619, 622

[56] References Cited

U.S. PATENT DOCUMENTS

| | | | |
|---|---|---|---|
| 5,196,452 | 3/1993 | Hwang et al. | 514/577 |
| 5,242,946 | 9/1993 | Guindon | 514/533 |
| 5,244,922 | 9/1993 | Burzynski et al. | 514/568 |
| 5,412,104 | 5/1995 | Afonso et al. | 514/63 |
| 5,434,188 | 7/1995 | Boschelli et al. | 514/617 |
| 5,461,075 | 10/1995 | O'Neill et al. | 514/622 |
| 5,512,596 | 4/1996 | Kim et al. | 514/568 |
| 5,547,976 | 8/1996 | Slater et al. | 514/410 |
| 5,668,178 | 9/1997 | Elslager et al. | 514/619 |

FOREIGN PATENT DOCUMENTS

WO 96/20915   7/1996   WIPO .

OTHER PUBLICATIONS

Dubey et al., "Synthesis of Substituted 1–Hydroxy–2–naphthanilides as Potential Cestodicidal Agents," *Journal of Medicinal Chemistry* 21(11):1178–1181, 1978.

Tripathy et al., "Synthesis of Some New Halogenated N–Thiazolyl Substituted Hydroxy Acid Amides and Their Use as Possible Fungicides," *Agricultural and Biological Chemistry* 37(6):1375–1383, 1973.

*Primary Examiner*—Jose' G. Dees
*Assistant Examiner*—Michael A. Williamson
*Attorney, Agent, or Firm*—Seed and Berry LLP

[57] ABSTRACT

Compounds having utility as anti-viral agents in general and, more specifically, to methods for treating a viral condition in an animal are disclosed. The compounds are naphthalene derivatives, and are preferably administered to the patient in the form of a pharmaceutical composition. Viruses treatable by the methods of this invention include viruses of the herpes virus family, such as cytomegalovirus, herpes simplex virus and human lymphotrophic herpes virus.

23 Claims, 24 Drawing Sheets

ANTI-VIRAL AGENTS AND METHODS RELATING TO THE USE THEREOF

TECHNICAL FIELD

The present invention relates generally to anti-viral agents and, more specifically, to methods for treating viral-associated conditions by administration to an animal in need of such treatment an anti-viral agent of this invention.

BACKGROUND OF THE INVENTION

In very general terms, a virus is an infectious agent made up of nucleic acid and protein that is inert outside a host cell. Upon infection, the virus causes a change in the nucleic acid and protein metabolism of the host cell. As a result, some or all of the viral genes are transcribed and/or translated, sometimes killing the host cell. A mature virus is termed a "virion" and consists of a shell of protein units arranged around a central core of nucleic acid. Viruses exist in a variety of forms, including icosahedral viruses having their envelope protein subunits arranged in the form of a polyhedron of 20 triangular faces, viruses having a cylindrical form, and viruses having a DNA-containing head and a long tail such as a bacteriophage. Viruses are divided into those that infect vertebrate animals, angiosperms, arthopods or bacteria. Only the bacteriophage possess an apparatus for injection of the nucleic acid into the host cell; other viruses are taken up intact by the host cell.

A representative example of an envelope icosahedral virus is cytomeglovirus (CMV), human (HCMV) or murine (MCMV), which contains a core of double-stranded DNA. More specifically, HCMV is a ubiquitous member of the herpes virus family that can induce a wide range of diseases, typically in newborns and immunocompromised adults. Nearly one percent of all live births in the United States are associated with congenital HCMV infection, with approximately 5 to 10 percent of infections resulting in significant neurological defects. In bone marrow transplant recipients, mortality due to HCMV pneumonia can be as high as forty percent. In addition, disseminated HCMV infection is common in immunocompromised patients, such as AIDS patients, and is frequently associated with conditions such as gastroenteritis and sight-threatening chorioretinitis.

In addition to CMV (also referred to as HHV-5), other types of herpes viruses have been described, including: herpes simplex virus (HSV-1) which can account for oral lesions such as fever blisters; human herpes virus (HHV-2) which is a sexually transmitted disease and produces lesions below the waistline, including veneral disease of the vagina and vulva, as well as herpetic ulcers of the penis; herpes varicella-zoster (HHV-3) which occurs clinically as either an acute form known as chickenpox or a chronic form termed shingles; Epstein-Barr virus (HHV-4) which has been linked to aplastic anemia, chronic fatigue syndrome, Burkitt's lymphoma, histiocytic sarcoma, hairy cell leukemia and immunocompromised patients; human B cell lymphotrophic virus (HHV-6) which is responsible for exanthem subitum; and HHV-7, a T cell lymphotrophic virus.

In order to successfully treat viral infection, particularly viral infection by viruses of the herpes family, there is a need for new agents that inhibit viral gene expression, as well as a need for methods of treating conditions associated with such infections. The present invention fulfills these needs and provides further related advantages.

SUMMARY OF THE INVENTION

In brief, this invention is directed to anti-viral agents, particularly anti-viral agents to viruses of the herpes virus family, and to methods for treating viral conditions associated with the same by administering to an animal in need thereof an effective amount of one or more anti-viral agents of this invention.

The anti-viral agents of this invention have the following general structure (I):

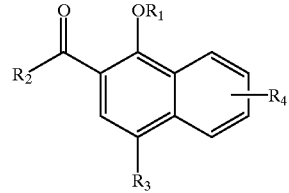

including pharmaceutically acceptable salts thereof, wherein $R_1$, $R_2$, $R_3$, and $R_4$ are as defined in the following detailed description.

In one embodiment, the virus is cytomeglovirus (CMV), and an anti-viral agent of this invention is administered to an animal in need thereof to treat CMV-associated conditions such as pneumonia, gastroenteritis and chorioretinitis. In another embodiment, the virus is a herpes virus (e.g., HSV-1 or HHV-2), and an anti-viral agent of this invention is administered to an animal in need thereof to treat viral-associated conditions such as lesions or herpetic ulcers.

In a further embodiment, a pharmaceutical composition is disclosed containing one or more anti-viral agents of this invention in combination with a pharmaceutically or prophylactically acceptable carrier or diluent. In the practice of this invention, the anti-viral agent is preferably administered to an animal in the form of a pharmaceutical composition.

These and other aspects of this invention will become evident upon reference to the attached figures and the following detailed description.

DETAILED DESCRIPTION OF THE INVENTION

Figure 1:
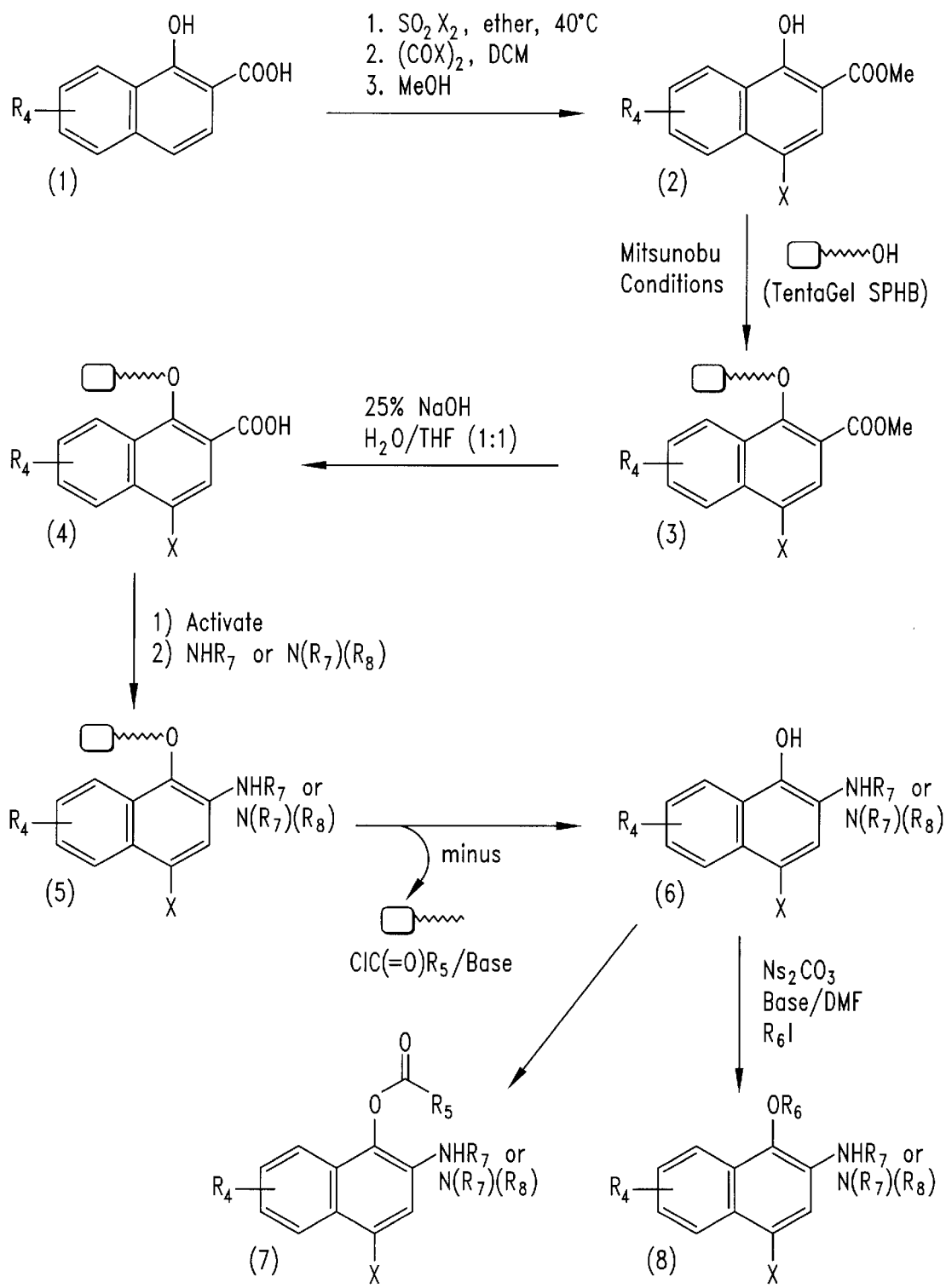
FIG. 1 illustrates a representative reaction scheme for making anti-viral agents of this invention.

As mentioned above, this invention is directed to anti-viral agents and to methods for treating one or more viral conditions associated with the same by administration of an anti-viral agent of this invention to an animal in need thereof. In a preferred aspect, the viral agents are of the herpes virus family, including (but not limited to) herpes simplex virus, human herpes virus, herpes varicella-zoster, Epstein-Barr virus, cytomegalovirus and human B cell lymphotrophic virus. The anti-viral agents of this invention are believed to function by effectively inhibiting viral gene expression. To this end, the anti-viral agents may inhibit viral gene transcription or translation, or may inhibit viral DNA replication.

The anti-viral agents of this invention are represented by the following structure (I):

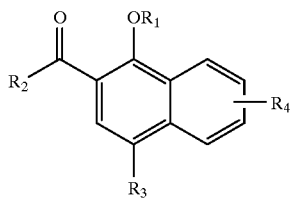

(I)

and pharmaceutically acceptable salts thereof, wherein
$R_1$ is selected from hydrogen, —$COR_5$ and —$R_6$;
$R_2$ is selected from hydroxy, —$OCOR_5$; —$OR_6$; —$NHR_7$ and —$N(R_7)(R_8)$;
$R_3$ is selected from hydrogen and halogen;
$R_4$ represents from one to four substituents, wherein each substituent is independently selected from halogen, hydroxy, amino, —$OR_5$ and —$R_6$;
$R_5$ is an unsubstituted or substituted $C_{1-8}$alkyl moiety;
$R_6$ is selected from an unsubstituted or substituted $C_{1-8}$alkyl moiety, an unsubstituted or substituted $C_{6-12}$aryl moiety and an unsubstituted or substituted $C_{7-12}$aralkyl moiety; and
$R_7$ and $R_8$ are independently selected from an unsubstituted or substituted $C_{6-12}$aryl moiety and an unsubstituted or substituted $C_{7-12}$aralkyl moiety.

As used herein, a "$C_{1-8}$alkyl" is a straight chain or branched, cyclic or non-cyclic, saturated or unsaturated carbon chain containing from 1 to 8 carbon atoms. In one embodiment, the $C_{1-8}$alkyl is a fully saturated, straight chain alkyl selected from methyl, ethyl, n-propyl, n-butyl, n-pentyl and n-hexyl. In another embodiment, the $C_{1-8}$alkyl is a fully saturated cyclic alkyl selected from (but not limited to) cyclopropyl, cyclobutyl, cyclopentyl, cyclohexyl, methylenecyclopropyl and methylenecyclohexyl. In still a further embodiment, the $C_{1-8}$alkyl is a fully saturated, branched alkyl selected from (but not limited to) isopropyl, sec-butyl, isobutyl, tert-butyl, isopentyl and isohexyl. In yet a further embodiment, the $C_{1-8}$alkyl is an unsaturated straight chain alkyl selected from (but not limited to) ethylenyl, propylenyl, 1-butenyl, 1-pentenyl and 1-hexenyl.

A "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl. In a preferred embodiment, the $C_{6-12}$aryl is phenyl.

A "$C_{7-12}$aralkyl" is an arene containing from 7 to 12 carbon atoms, and has both aliphatic and aromatic units. In one embodiment, the $C_{7-12}$aralkyl is selected from (but not limited to) benzyl, ethylbenzyl, propylbenzyl and isobutylbenzyl.

A "substituted" $C_{1-8}$alkyl, $C_{6-12}$aryl or $C_{7-12}$aralkyl moiety is a $C_{1-8}$alkyl, $C_{6-12}$aryl or $C_{7-12}$aralkyl moiety having one or more hydrogens replaced with a substituent.

A "substituent" is a moiety selected from halogen, —OH, —R, —OR, —COOH, —COOR, —COR, —$CONH_2$, —$NH_2$, —NHR, —NRR, —SH, —SR, —SOOR, —SOOH and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

A "$C_{3-12}$heterocycle" is a compound that contains a ring made up of more than one kind of atom, and which contains 3 to 12 carbon atoms, including (but not limited to) pyrrolyl, furanyl, thiophenyl, imidazolyl, oxazolyl, thiazolyl, pyrazolyl, pyrrolidinyl, pyridinyl, pyrimidinyl and purinyl.

A "$C_{4-16}$heterocyclealkyl" is a compound that contains a $C_{3-12}$heterocycle linked to a $C_{1-8}$alkyl.

A "halogen" is selected from fluoro, chloro, bromo and iodo.

In one embodiment, the anti-viral agents of this invention have the following structure (II):

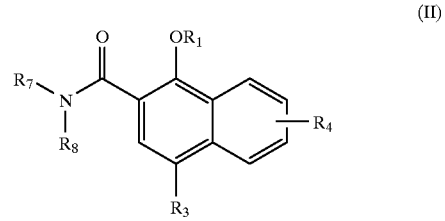

(II)

wherein $R_1$, $R_3$, $R_4$, $R_7$ and $R_8$ are as defined above.

In a preferred embodiment, $R_3$ is halogen, $R_4$ and $R_7$ are hydrogen, and $R_8$ is a substituted phenyl, yielding the following structure (III):

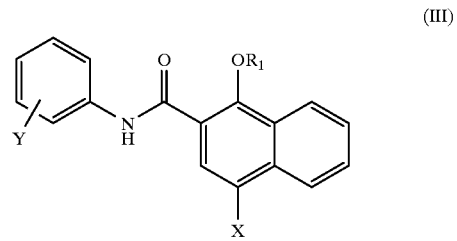

(III)

wherein X is a halogen and Y is one or more substituents as defined above.

In further preferred embodiments of structure (III), $R_1$ is hydrogen and X is chloro, including (but not limited to) the following structures (IV) and (V):

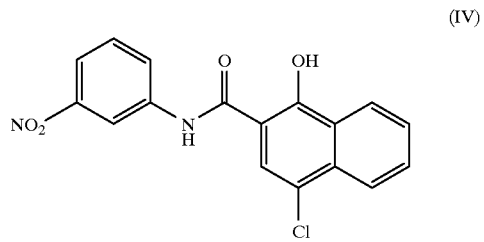

(IV)

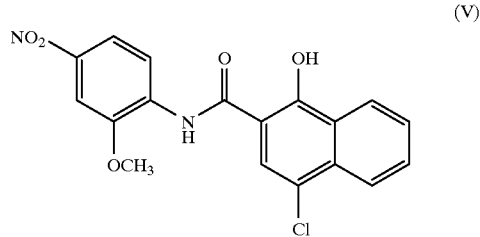

(V)

The compounds of this invention may be made by one skilled in organic synthesis by known techniques, as well as by the synthetic routes disclosed herein. For example, representative anti-viral agents of this invention may be synthesized on a solid support by the reaction scheme set forth in FIG. 1. As illustrated in FIG. 1, an appropriate 1-hydroxy-4-halo-2-naphthoic acid ester (2) may be generated from the corresponding 1-hydroxy-2-naphthoic acid (1). Naphthoic acid ester (2) may then be bound to a suitable solid support, such as TentaGel SPHB resin (Advanced Chem Tech, Louisville, Ky.) under Mitsunobu conditions (5 equivalents of $Ph_3P$, diethylazidodicarboxylate in N-methyl morpholine), to yield the bound naphthoic acid ester (3). After saponification of bound naphthoic acid ester (3) with a solution of 5% NaOH (aq)/THF (1:1) followed by 2.5% HCl in THF, resin-bound 4-halo-2-naphthoic acid (4) is generated and added to one or more dispersion tubes (e.g., 200 mgs/tube).

The dispersion tubes are placed into a stock solution of diisopropylcarbodiimide, 1-hydroxybenzotriazole and diispropylethylamine in DMF for 2 hours to activate the carboxylic acid. The dispersion tubes are then lowered into one or more test tubes, each test tube containing a different amine or aniline derivative (5 equivalents) in DMF (2 ml). The reaction is allowed to proceed for 18 hours, then the excess reagents are washed away leaving only clean, resin-bound 2-amino-4-halonaphthalene products (5). The dispersion tubes are then placed into one or more further test tubes (tared by the benchmate) and treated with a stock solution of 20% TFA in dichloromethane, cleaving product (5) from the resin. This provides one (or more) anti-viral agents of this invention (6) (3–7 mgs of each that are >90% pure as indicated by HPLC), where $R_1$ is hydrogen, $R_2$ is —$NHR_7$ or —$N(R_7)(R_8)$, $R_3$ is X (i.e., halogen), and $R_4$ is a substituent.

Anti-viral agents of this invention where $R_3$ is hydrogen may be made by employing a non-halogenated equivalent of the naphthoic acid ester (2) of FIG. 1. Anti-viral agents where $R_1$ is —$COR_5$ (7) may be made by acylation with the appropriate acid chloride in a solvent such as dichloromethane using a base such as triethylamine. Compounds where $R_1$ is $R_6$ (8) may be made by alkylation using a base such as cesium carbonate in a polar solvent like DMF, followed by treatment with alkyliodide. Further, anti-viral agents where $R_2$ is hydroxy may be generated directly from resin-bound 4-halo-2-naphthoic acid (4), and anti-viral agents where $R_2$ is —$OCOR_5$ or —$OR_6$ may be generated by treating activated (4) with $R_6OH$, then cleavage from the resin to provide compounds where $R_2$ is —$OR_6$. Compounds where $R_2$ is —$OCOR_5$ may be prepared by treating (6) with $(R_5CO)_2O$ in a solvent such as dichloromethane in the presence of a tertiary amine base such as triethylamine.

Once synthesized, the anti-viral agents or compounds of this invention may be formulated for administration to an animal, particularly a warm-blooded animal, by a variety of techniques known to those skilled in the art. In one embodiment, the compound is in the form of a pharmaceutical composition for prophylactic or therapeutic use, and which contains at least one compound of this invention in combination with a pharmaceutically acceptable carrier or diluent. The compound is present in the composition in an amount which, upon administration to the animal, is effective in preventing or treating the condition of interest. Preferably, the composition includes a compound of this invention in an amount ranging from 0.01 mg to 250 mg per dosage, depending upon the route of administration, and more preferably from 1 mg to 60 mg. Appropriate concentrations, dosages and modes of administration may be readily determined by one skilled in the art.

Suitable carriers or diluents are familiar to those skilled in the formulation field. For compositions formulated as liquid solutions, acceptable carrier or diluents include saline and sterile water, and may optionally include antioxidants, buffers, bacteriostats and other common additives. The compositions of this invention may also be formulated as pills, capsules, granules or tablets which contain, in addition to the compound of this invention, diluents, dispersing and surface active agents, binders and lubricants. One skilled in the art may further formulate the compounds of this invention in any appropriate manner, and in accordance with accepted practices, such as those disclosed in *Remington's Pharmaceutical Sciences,* Gennaro, Ed., Mack Publishing Co., Easton, Pa., 1990 (incorporated herein by reference).

In another embodiment, the present invention provides methods for treating a viral condition. Such methods include administering a compound of this invention to an animal in need thereof in an amount sufficient to treat the viral-associated condition. Such methods include both local and systemic administration of a compound of this invention, preferably in the form of a composition as disclosed above. As used herein, systemic administration includes oral and parental methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. For parental administration, the compounds of the present invention may be prepared in aqueous injectable solutions which may contain, in addition to the compound of this invention, buffers, antioxidants, bacteriostats and other additives commonly employed in such solutions. For local administration, including (but not limited to) topical application, suitable compositions may be readily formulated as solutions, creams, gels, powders or ointments by known techniques.

The anti-viral agents of this invention may be assayed for their ability to inhibit viral replication by any number of known methods. In the case of CMV, the anti-viral agents may be screened in the high-throughput assay as set forth in Examples 1–5. Additional assays known to those skilled in the art may be employed for screening activity against other viruses. For example, assays which detect a reduction in virus yield may be employed, such as the plaque assay disclosed in Example 6.

The following examples are presented for purpose of illustration, not limitation.

EXAMPLES

Example 1

Preparation of Transfected Cells

This Example illustrates the preparation of cell lines carrying an integrated plasmid that contains a reporter gene under the control of a cytomegalovirus promoter.

A. Plasmid Construction

1. MIEP-luc

The MIEP promoter sequence, from position −1145 to +122, was amplified by PCR using plasmid pSE as a template. The primers are: 5'-CGGGGTACCGCTGCAGTGAATAATAAAATG-3' (sense primer), and 5'CGGGGTACCGTCACTCTTGGCACGGGGAATC-3' (antisense primer). These oligo primers introduced a KpnI restriction site at the 5' and 3' end of MIEP promoter fragment. The KpnI digested PCR fragment was inserted into KpnI digested pGL2-basic luciferase reporter plasmid (Promega, Madison, Wis.). The promoter direction was determined and PCR fidelity of the promoter sequence was confirmed by sequencing.

2. Pol-luc

The Pol promoter sequence, from position −425 to +15, was amplified by PCR using cosmid pCM1058 (Peter Ghazal) as template. The primers are: 5'-CCCAAGCTTGGGGAATTCAACTCGTACAAGCAG-3' (sense primer), and 5'-CCCAAGCTTGGGTCAGACGACGGTGGTCCC-3' (antisense primer). These oligo primers introduced a HindIII restriction site at the 5' and 3' end of Pol promoter fragment. The HindIII digested PCR fragment was inserted into HindIII digested pGL2-basic luciferase reporter plasmid (Promega, Madison, Wis.). The promoter direction was determined and PCR fidelity of the promoter sequence was confirmed by sequencing.

3. pp28-luc

The pp28 promoter sequence, from position −609 to +106, was amplified by PCR using cosmid pCM1 (Peter Ghazal, Scripps Research Institute) as a template. The oligonucleotide primer sequences are:

5'-AAAGGTACCGCCGGCGTCTCGCCGGGCATC-3' (sense primer), and

5'-AAAAAGCTTGCCGGCCCAGCAGCTCGGGCG-3' (antisense primer).

Figure 2A:
FIG. 2 is a diagram illustrating CMV promoter/reporter gene constructs (pp28-luc, pol-luc and MIEP-luc).
Figure 2B:
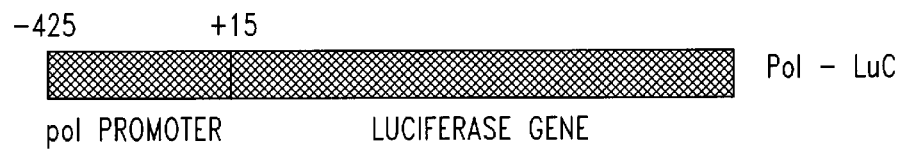
Figure 2C:
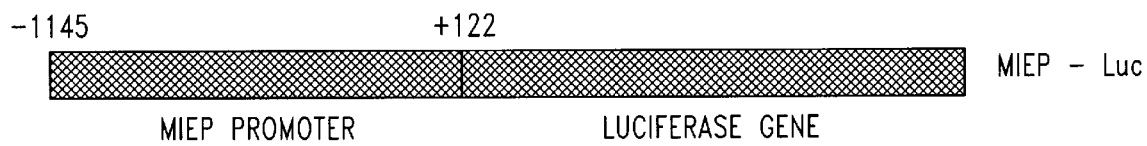

These oligonucleotides primers introduced a KpnI restriction site at the 5'-end and a HindIII site at the 3'-end of the pp28 promoter fragment. Unique sites, KpnI and HindIII allowed directional cloning into the pGL2-basic luciferase reporter plasmid (Promega, Madison, Wis.), resulting in the pp28-luc promoter construct shown in FIG. 2. The PCR fidelity of the pp28 promoter sequence was confirmed by sequencing.

B. Establishment of Stable Cell Lines

The HCMV permissive human glioblastoma cell line U373 MG was transfected with the constructs described above. Conditions for cell growth were as described in Baracchini et al., Virol. 188:518–529, 1992. The pp28-luciferase reporter and pSV2Neo selection plasmid were cotransfected into U373 MG cells by the calcium phosphate method. Transfectants were selected in medium containing 0.6 mg/ml G418 on the third day after transfection. G418-resistant clones were expanded and $3 \times 10^4$ cells seeded in triplicate in a 96 well plate.

Cells were infected with HCMV (Towne strain, obtained from American Type Culture Collection, Rockville, Md.) at 5–10 pfu/cell. 48 hours postinfection, cells were harvested and assayed for luciferase activity as follows. Culture media was removed and the cells were rinsed once with PBS buffer without $Ca^{++}$ and $Mg^{++}$ (137 mM NaCl, 2.7 mM KCl, 4.3 mM $Na_2HPO_4$ and 1.4 mM $KH_2PO_4$). Sixty microliters of 1× Lysis buffer containing 25 mM Tris-phosphate, pH 7.8, 2 mM DTT, 2 mM 1,2-diaminocyclohexane-N,N,N',N'-tetraacetic acid, 10% glycerol and 1% Triton X-100 (Promega Cell Culture Lysis Buffer, Madison, Wis.) was added. After incubation at room temperature for 15 minutes, 40 μL of cell lysate was transferred to a black 96-well plate and 50 μL of luciferase substrate (Promega, Madison, Wis.) was added to each well. Plates were read immediately in a Packard TopCount™ (Packard, Hartford, Conn.). Clones showing high luciferase inducibility were further analyzed by PCR to ascertain the integrity of the reporter transcriptional unit integrated into the genomic DNA.

Example 2

Analysis of Reporter Gene Expression upon Viral Infection

This Example illustrates the kinetic analysis of reporter gene expression, using the cell lines prepared in Example 1, upon HCMV infection.

Figure 3:
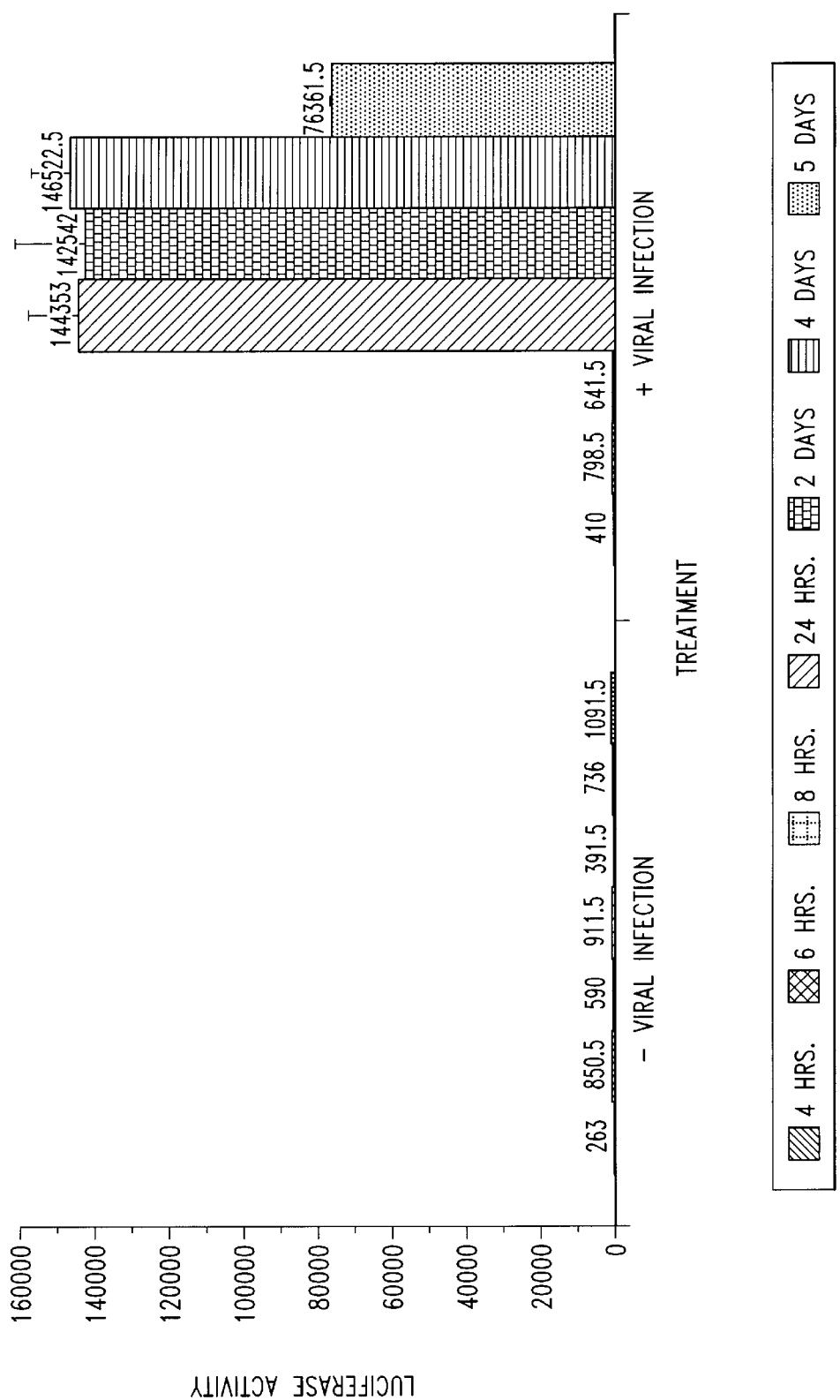
FIG. 3 is a graph presenting the results of a kinetic analysis of luciferase induction upon viral infection in the MIEP-luc stable cell line. Luciferase activity is shown at 4 hours, 6 hours, 8 hours, 24 hours, 2 days, 4 days and 5 days, with (columns 8–14) and without (columns 1–7) HCMV infection.
Figure 4:
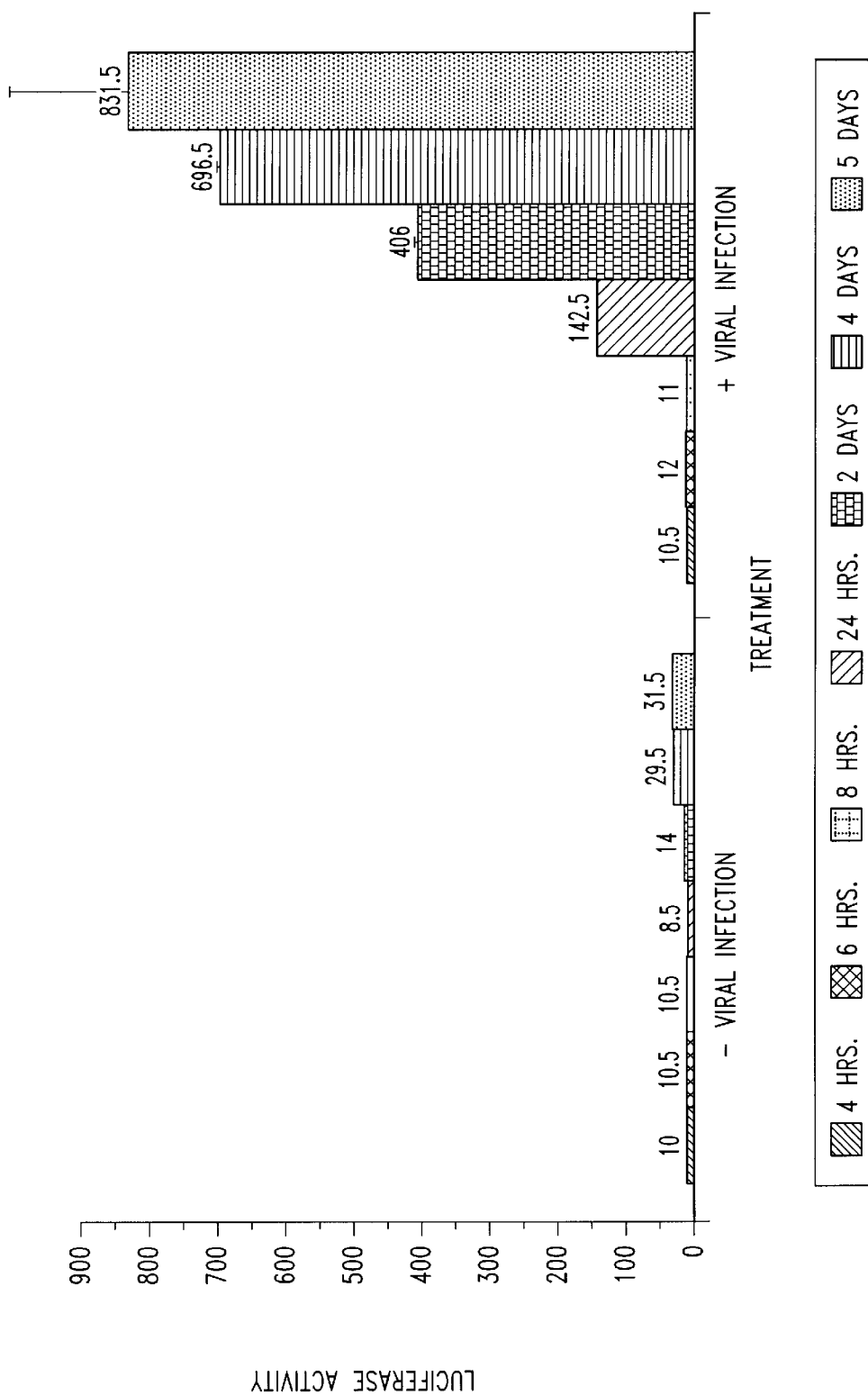
FIG. 4 is a graph presenting the results of a kinetic analysis of luciferase induction upon viral infection in the pol-luc stable cell line. Luciferase activity is shown at 4 hours, 6 hours, 8 hours, 24 hours, 2 days, 4 days and 5 days, with (columns 8–14) and without (columns 1–7) HCMV infection.
Figure 5:
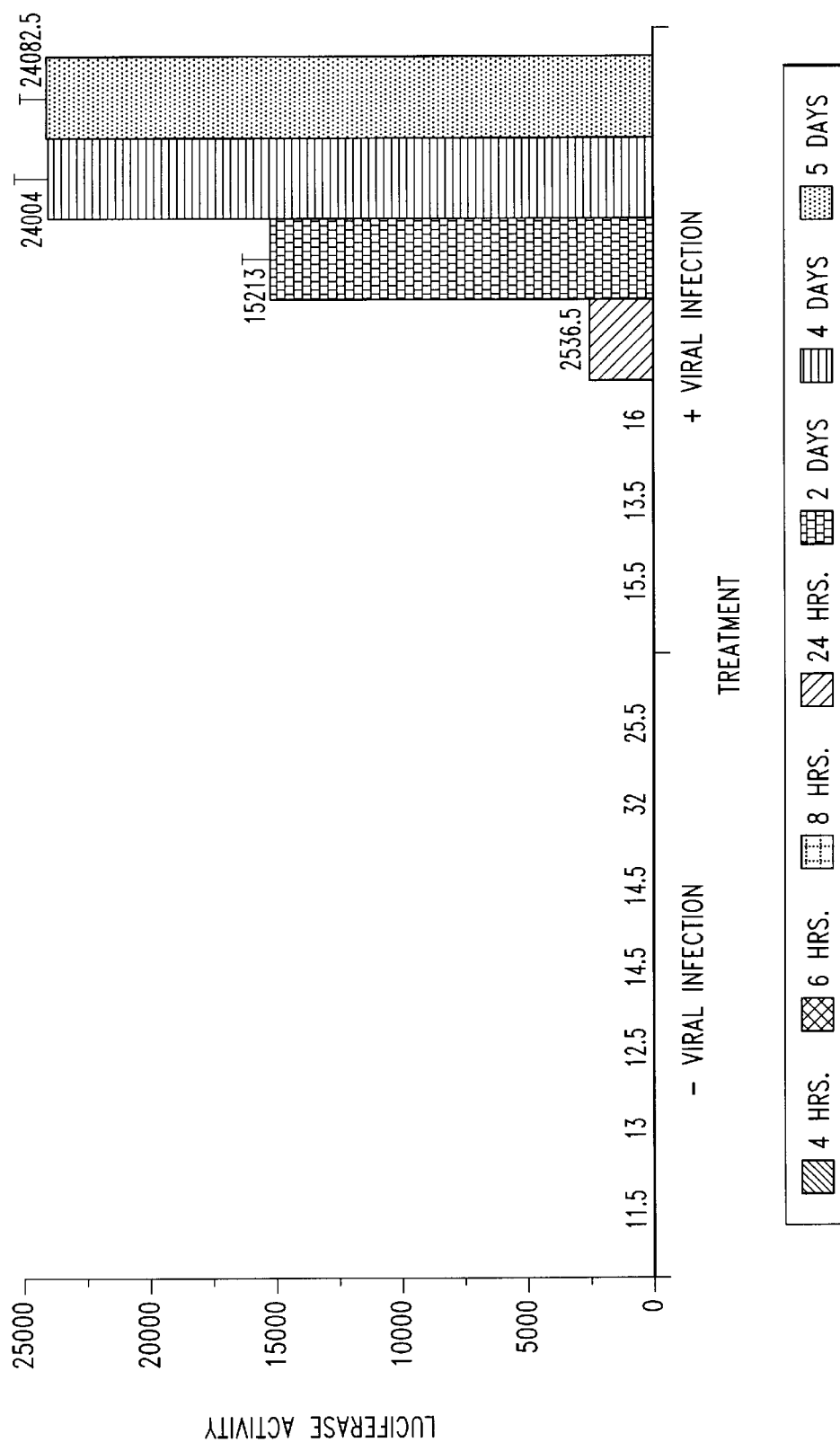
FIG. 5 is a graph presenting the results of a kinetic analysis of luciferase induction upon viral infection in the pp28-luc stable cell line. Luciferase activity is shown at 4 hours, 6 hours, 8 hours, 24 hours, 2 days, 4 days and 5 days, with (columns 8–14) and without (columns 1–7) HCMV infection.

Cell lines prepared as described above were infected with the Towne strain of HCMV (ATCC Accession No. VR-977) at a multiplicity of infection of 5–10 pfu/cell, and luciferase activity was measured at various times over a period of 5 days. The results are presented in FIGS. 3–5. For each cell line, luciferase activity was detected at 24 hours. The MIEP-luc cell line showed maximal activity at 24 hours—4 days, with decreased activity at 5 days post-infection (FIG. 3). The pol-luc (FIG. 4) and pp28 (FIG. 5) cell lines showed a gradual increase at 48 hours, peaking at 4–5 days postinfection. In each case, the kinetics of gene expression were similar to that expected for the endogenous viral gene.

These data indicate that luciferase expression regulated through the HCMV promoter tested is very low in permissive cells but is strongly activated upon viral infection. However, if the transfected cells were infected with the UV-treated virus, luciferase activity was not detected (data not shown). Due to the short half-life of luciferase we concluded that the increase in luciferase activity reflects activation of transcription and not simply accumulation of the reporter protein. These results indicate that activation of these promoters required viral gene expression, and that the promoters respond to viral infection similarly to promoters within the context of the viral genome.

Figure 6A:
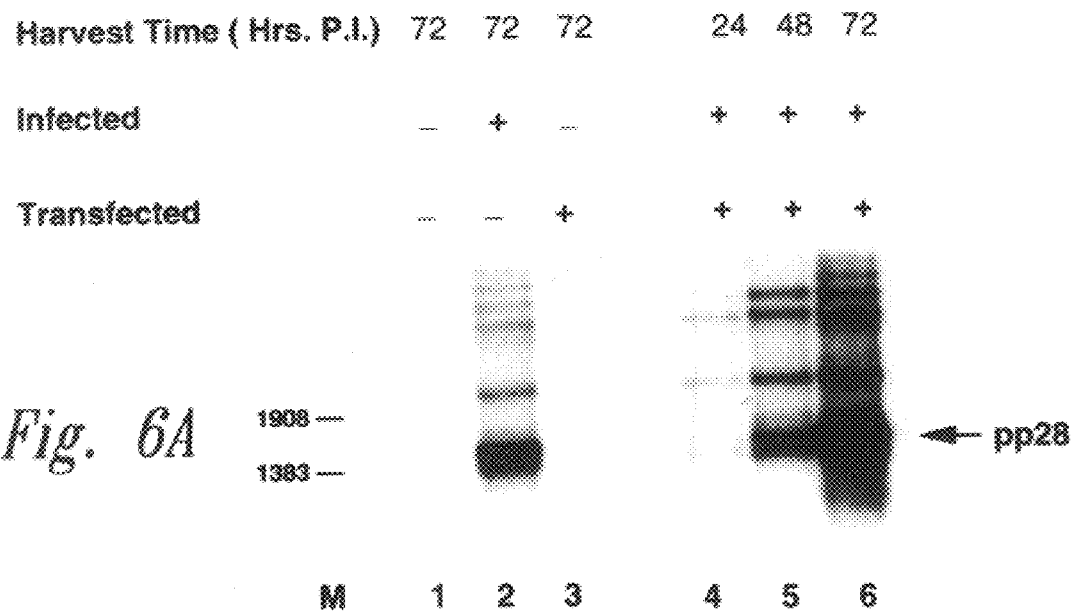
FIG. 6 is an autoradiogram showing the results of a Northern blot analysis, using luciferase (panel B) and pp28 (panel A) gene fragments as probes, with mRNA isolated from uninfected, untransfected cells (lane 1), infected only cells (lane 2), transfected only cells (lane 3), and transfected, HCMV-infected cells 24 hours (lane 4), 48 hours (lane 5) and 72 hours (lane 6) post infection.
Figure 6B:
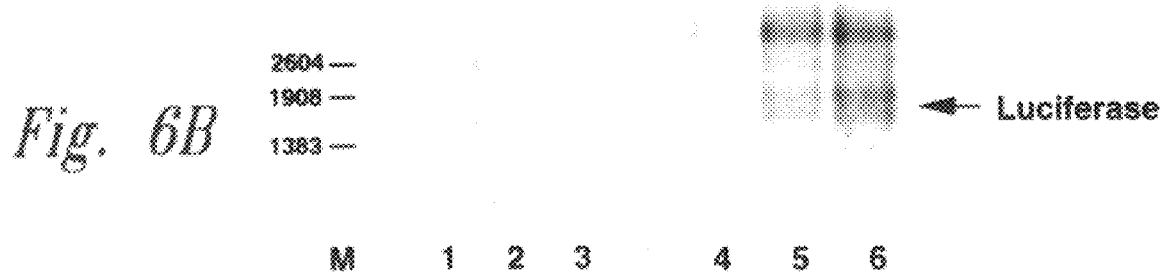

The expression patterns for the pp28-luc gene and the endogenous pp28 gene were also compared using Northern blot analysis, with luciferase and pp28 gene fragments as probes (FIG. 6). Transfected and infected U373 MG cells were processed for messenger RNA as indicated by the manufacturer (Stratagene, La Jolla, Calif.), and equal aliquots of mRNA were subjected to Northern blot analysis. Probes were labeled with $\alpha$-$^{32}$P-dCTP (3000 Ci/mmol, Amersham, Arlington Heights, Ill.) using Prime-It RmT random primer labeling kit (Stratagene, La Jolla, Calif.). Blots were hybridized to the radiolabeled probes for each gene using a QuikHyb hybridization solution following the manufacturer's protocol (Stratagene, La Jolla, Calif.).

This analysis showed that pp28 mRNA was detectable at 24 hours and increased at 48 and 72 hours progressively (FIG. 6, panel A, lanes 4, 5, and 6, respectively). In contrast, no luciferase mRNA could be detected in cells infected only (FIG. 6, panel B, lane 2), or transfected only (FIG. 6, panel B, lane 3) compared to mock-treated control cells (FIG. 6, panels A and B, lane 1). These results suggest that the pp28 promoter, out of the viral genome context, behaves similarly to its endogenous counterpart.

Figure 7A:
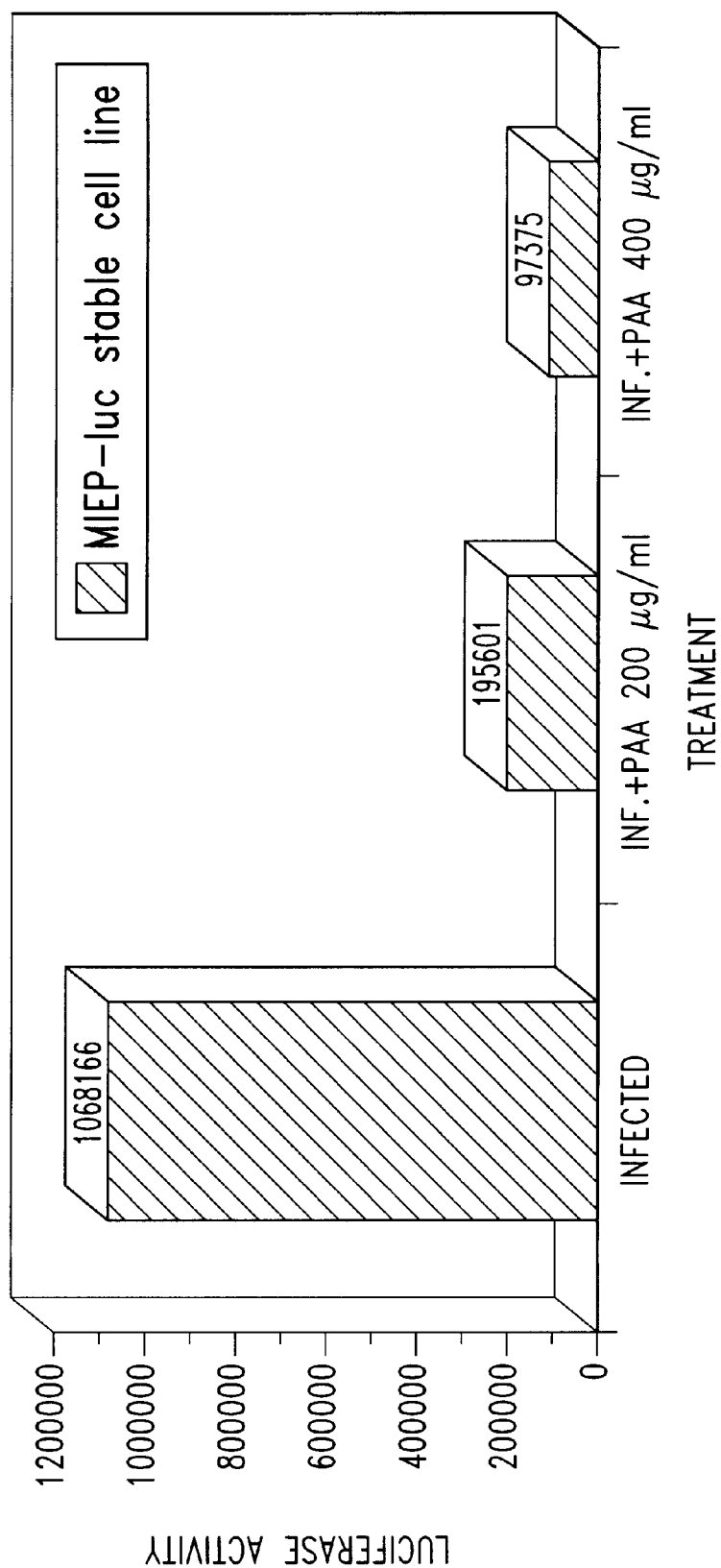
FIG. 7, panel A, is a graph depicting the luciferase activity detected in MIEP-luc cells 48 hours after infection with HCMV in the absence of viral DNA replication inhibitor (column 1), in the presence of 200 μg/mL phosphonoacetic acid (column 2) and in the presence of 400 μg/mL phosphonoacetic acid (column 3). Panel B is an autoradiogram showing the results of a Northern analysis using mRNA prepared from MIEP-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, IE-specific mRNA and beta-actin mRNA as indicated by the arrows. Panel C is an autoradiogram showing the results of a Western analysis using protein lysates prepared from MIEP-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase and IE proteins, as indicated by the arrows.
Figure 7B:
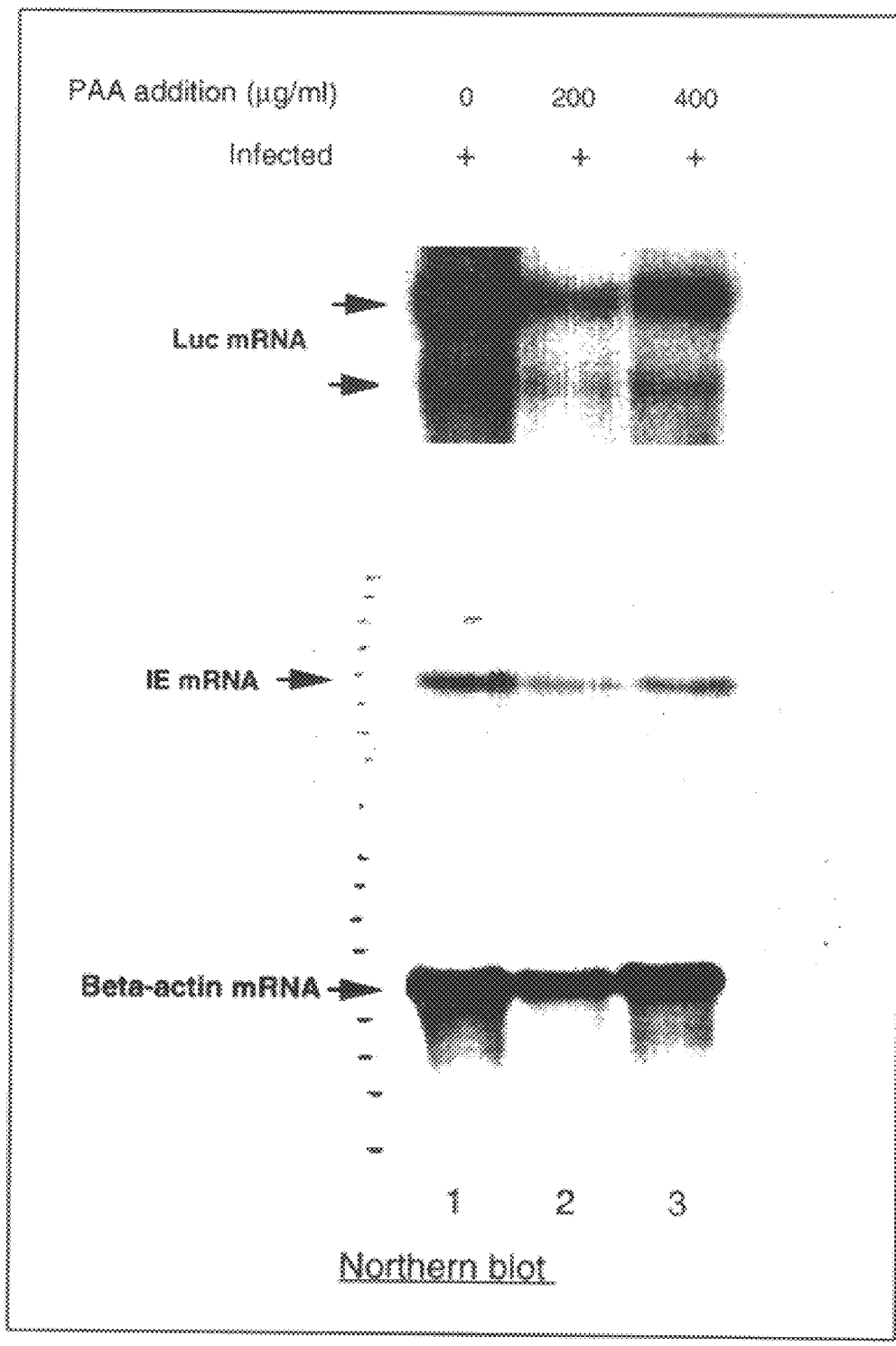
Figure 7C:
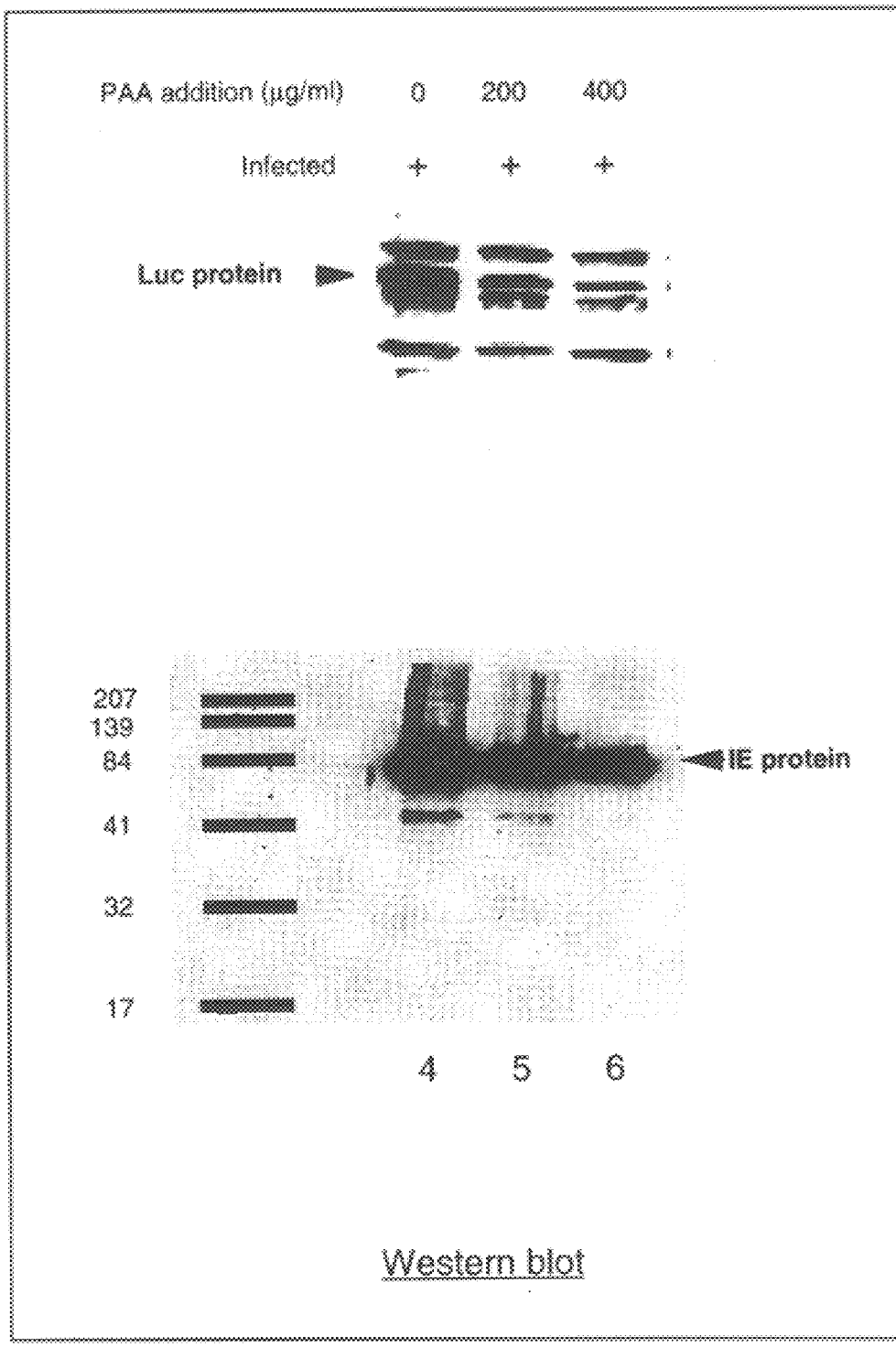
Figure 8A:
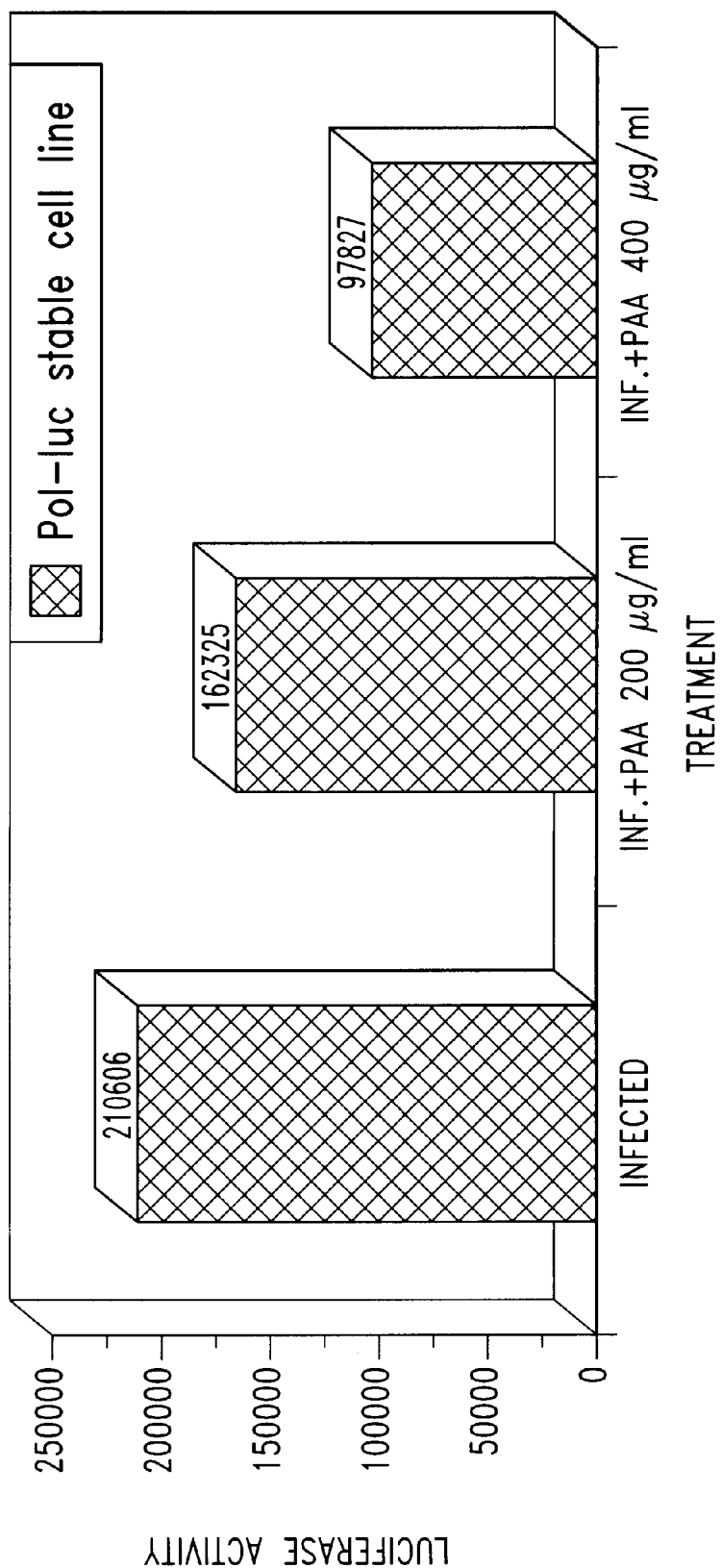
FIG. 8, panel A, is a graph depicting the luciferase activity detected in pol-luc cells 48 hours after infection with HCMV in the absence of viral DNA replication inhibitor (column 1), in the presence of 200 μg/mL phosphonoacetic acid (column 2) and in the presence of 400 μg/mL phosphonoacetic acid (column 3). Panel B is an autoradiogram showing the results of a Northern analysis using mRNA prepared from pol-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, pol specific mRNA and beta-actin mRNA as indicated by the arrows. Panel C is an autoradiogram showing the results of a Western analysis using protein lysates prepared from pol-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase, as indicated by the arrow.
Figure 8B:
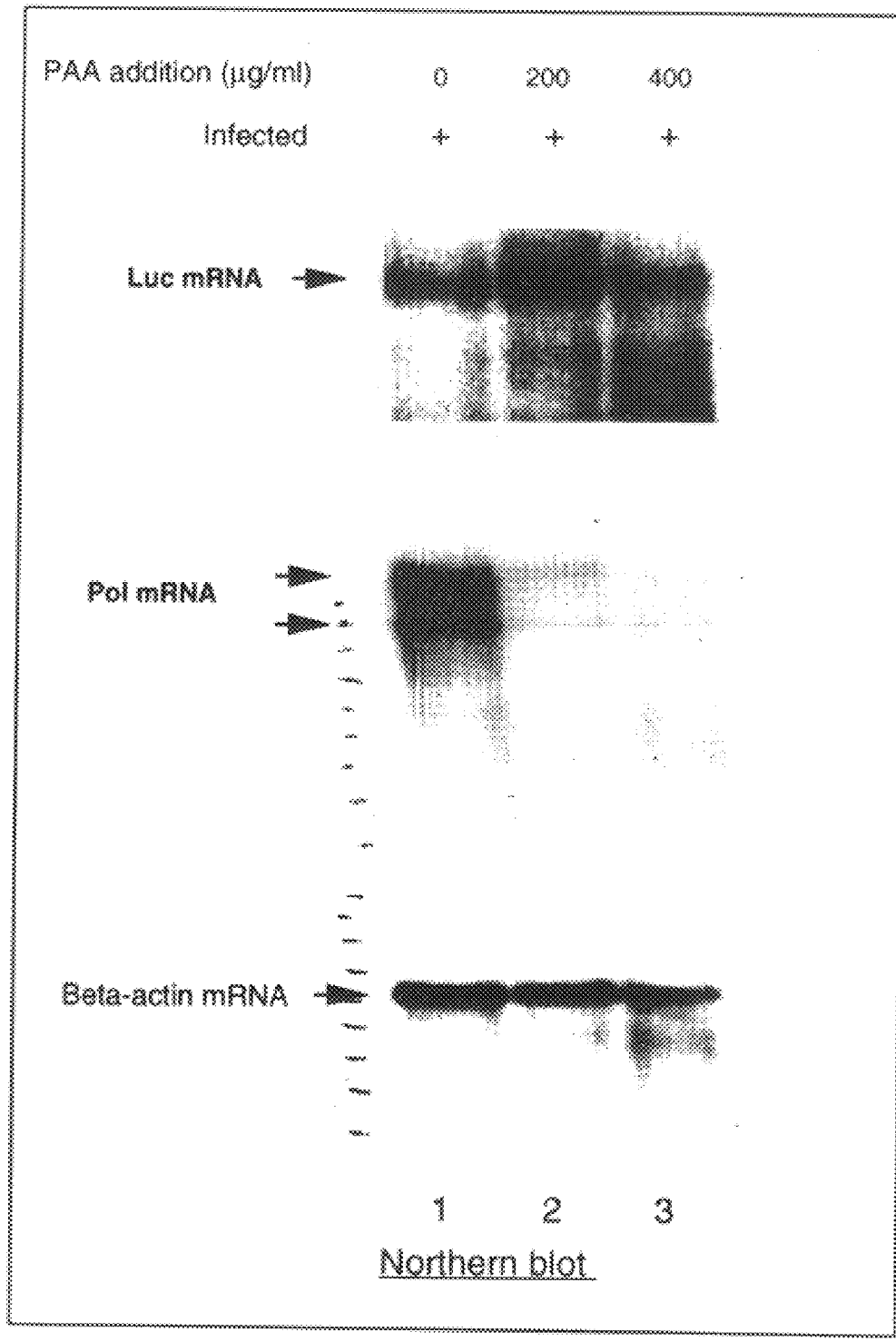
Figure 8C:
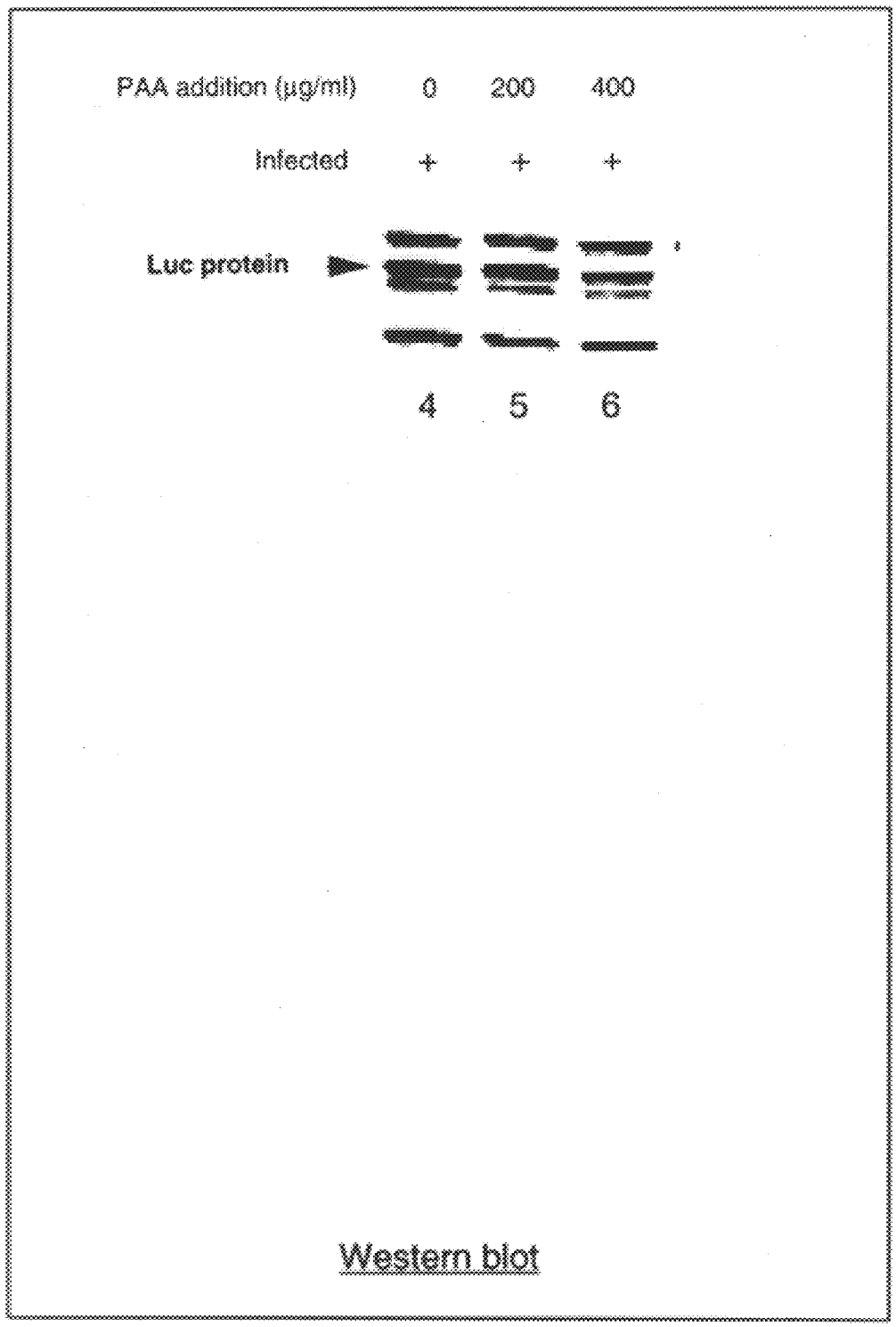
Figure 9A:
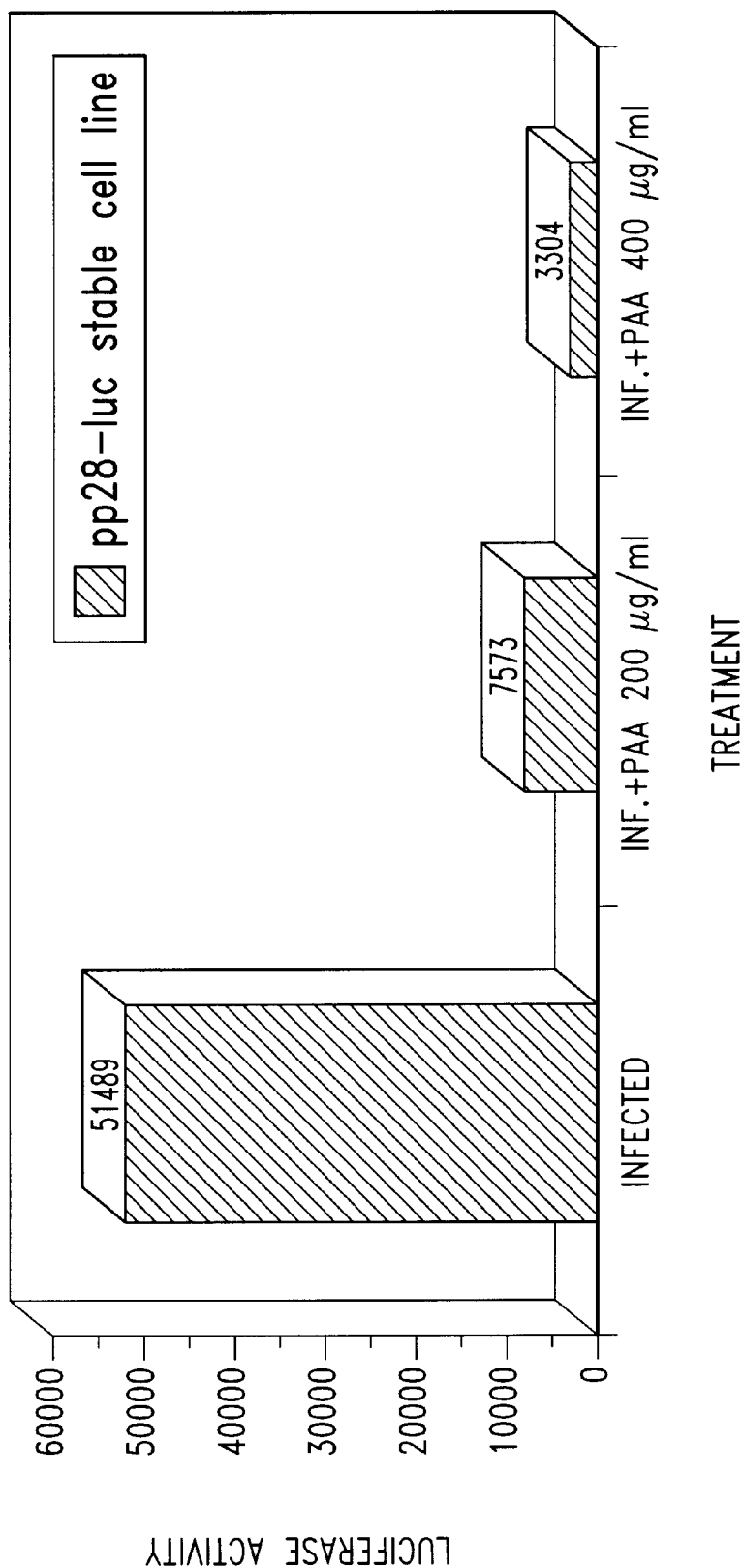
FIG. 9, panel A, is a graph depicting the luciferase activity detected in pp28-luc cells 48 hours after infection with HCMV in the absence of viral DNA replication inhibitor (column 1), in the presence of 200 μg/mL phosphonoacetic acid (column 2) and in the presence of 400 μg/mL phosphonoacetic acid (column 3). Panel B is an autoradiogram showing the results of a Northern analysis using mRNA prepared from pp28-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, pp28 mRNA and beta-actin mRNA as indicated by the arrows. Panel C is an autoradiogram showing the results of a Western analysis using protein lysates prepared from pp28-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase and pp28 proteins, as indicated by the arrows.
Figure 9B:
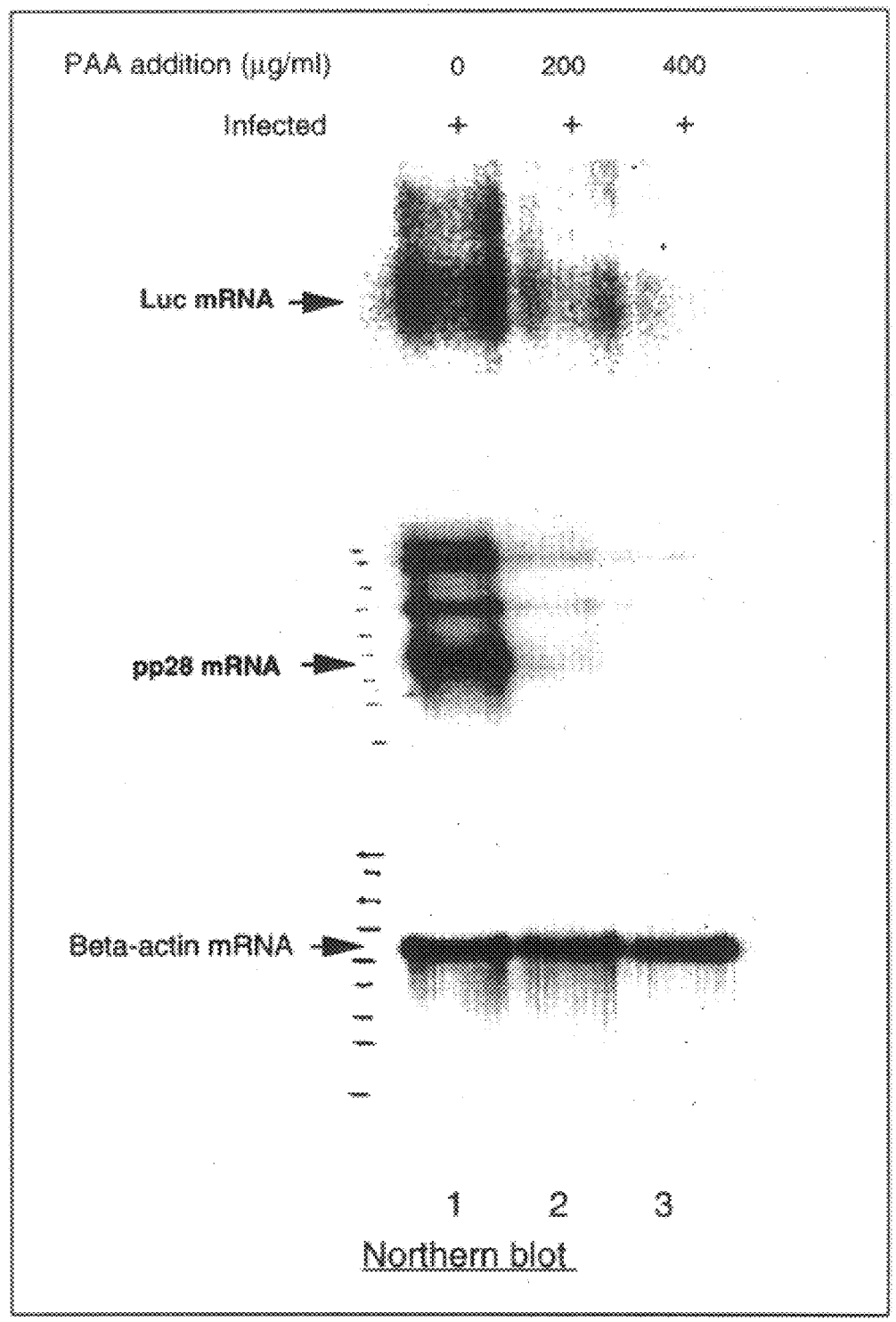
Figure 9C:
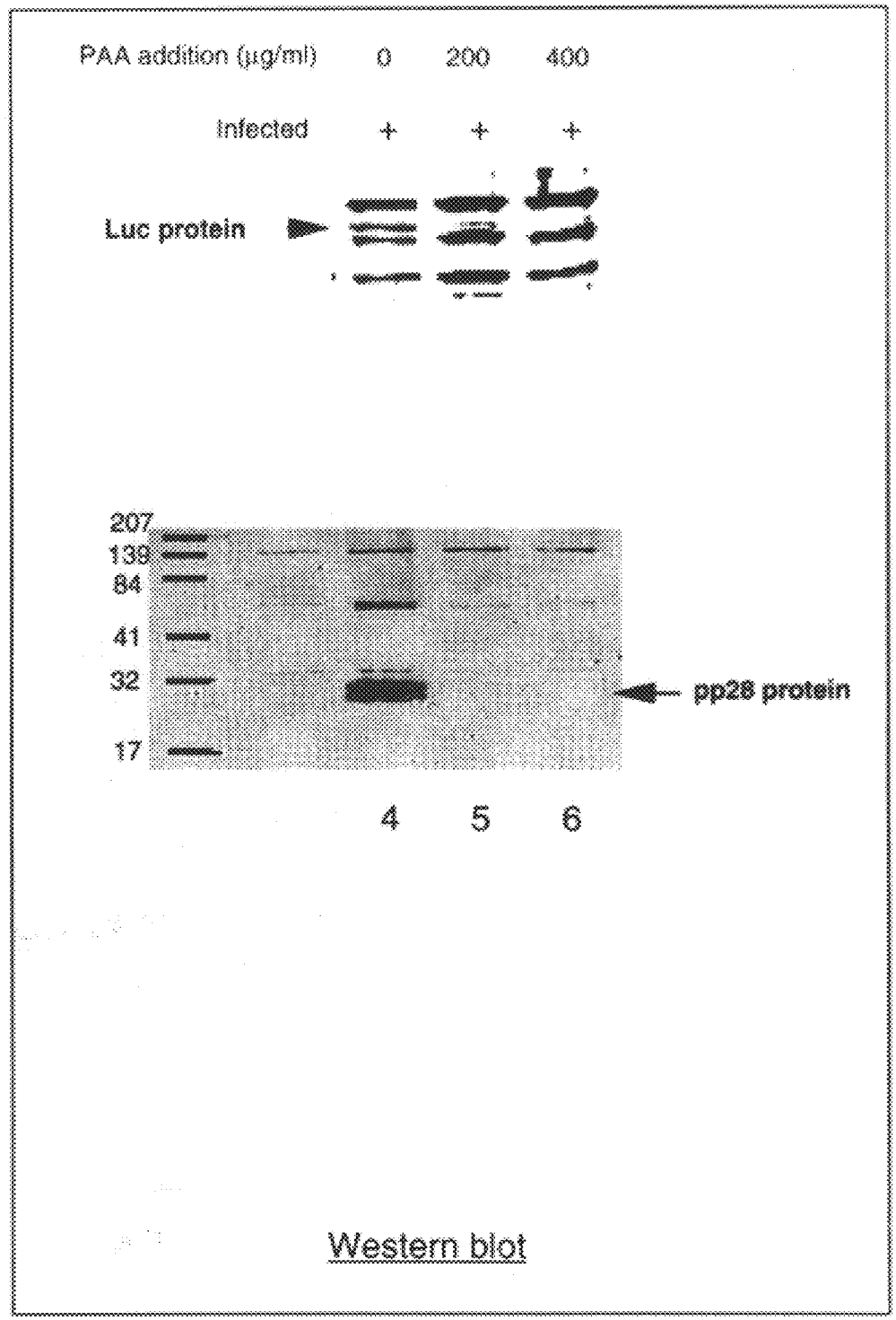

The response of the integrated reporter plasmids to HCMV infection was also examined in the presence and absence of the well characterized viral DNA inhibitor phosphonoacetic acid (PAA, Sigma, St. Louis, Mo., 99.7 purity). The results are presented in FIG. 7 (P-luc), FIG. 8 (pol-luc) and FIG. 9 (pp28-luc). Cells were seeded into a 96 well plate in G418 selection media. The following day, cells were treated in the absence (lanes 1 and 4, panels B and C) or presence of PAA at 200 μg/mL (lanes 2 and 5, panels B and C) and 400 μg/mL (lanes 3 and 6, panels B and C). Cells were then superinfected with HCMV at 10 pfu/cell. Forty-eight hours post-infection, cells were harvested and isolated for either mRNA preparation, protein lysates or the luciferase assay. Luciferase activity measured as described above is shown in panels A of FIGS. 7–9. Northern analyses were performed on mRNA using probes for luciferase, MIEP-, pol- or pp28-specific mRNA and beta-actin mRNA to quantitate the amount of mRNA in each lane (panels B). Protein lysates were used for western blot analysis using antibody specific against luciferase (panels C). The inhibitory concentration of PAA (200–400 μg/ml) was not toxic to the U373 MG cells based on MTS cytotoxicity assay (data not shown). Viral DNA replication in presence of PAA was inhibited by nearly 90 percent as determined by dot blot analysis in three different stable clones (data not shown). The results indicate that inhibition of viral DNA replication has the same effect on luciferase expression as it does on endogenous viral gene expression. Accordingly, the cell lines can be used to identify inhibitors of the cascade of gene expression that occurs during natural viral infection.

Example 3

Specificity of Induction of Reporter Gene Expression

This Example illustrates the ability of the cell lines described in Example 1 to differentiate among different herpes viruses.

Figure 10A:
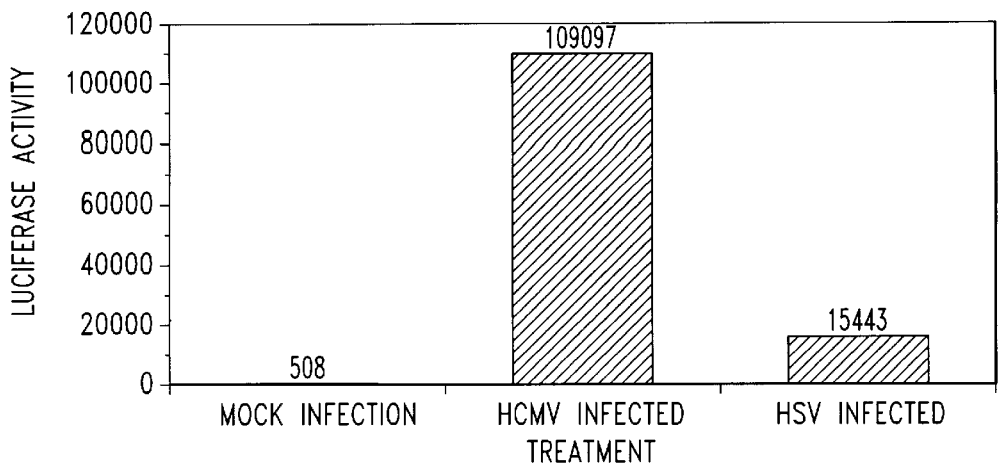
FIG. 10, panel A, is a graph depicting the luciferase activity detected in MIEP-luc cells without HCMV infection (column 1), after HCMV infection (column 2) and after HSV-1 infection (column 3). Panel B is a graph depicting the luciferase activity detected in pol-luc cells without HCMV infection (column 1), after HCMV infection (column 2) and after HSV-1 infection (column 3). Panel C is a graph depicting the luciferase activity detected in pp28-luc cells without HCMV infection (column 1), after HCMV infection (column 2) and after HSV-1 infection (column 3).
Figure 10B:
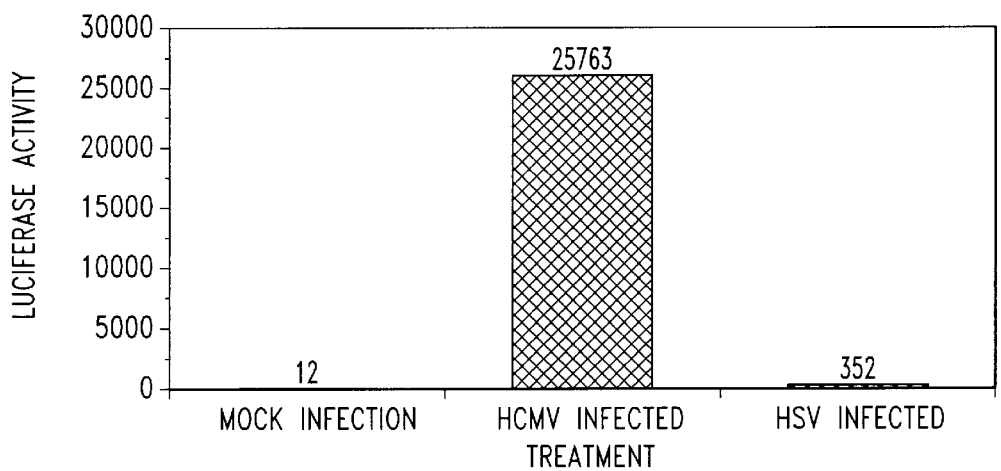
Figure 10C:
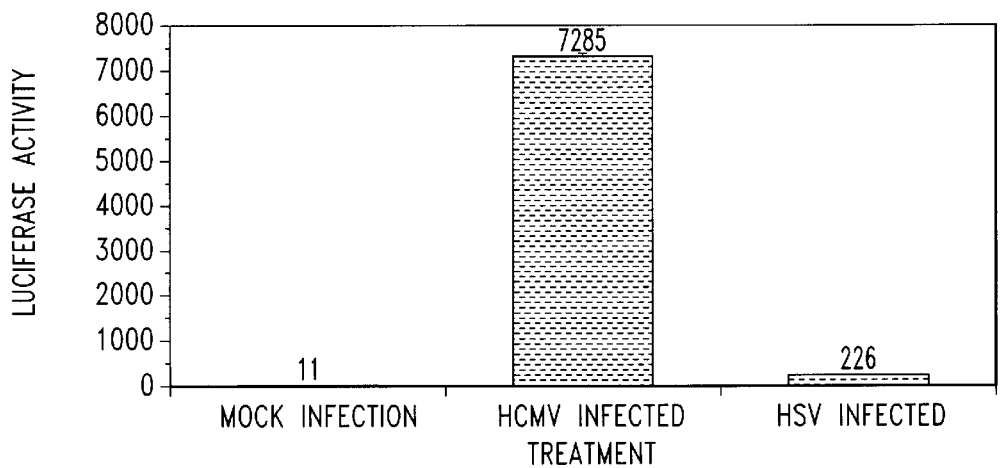
Figure 11:
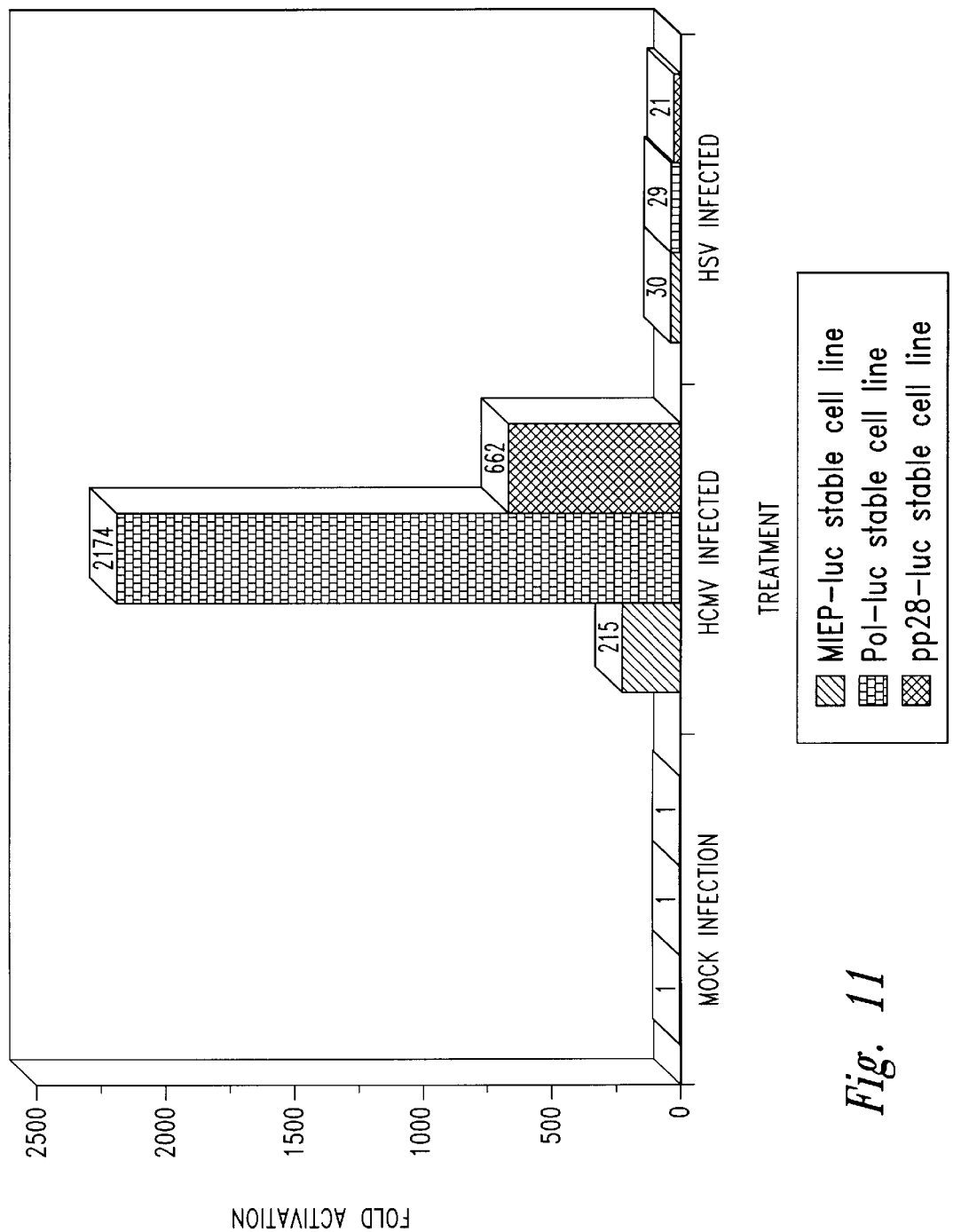
FIG. 11 is a graph showing the fold activation of luciferase activity for the MIEP-luc (columns 1, 4 and 7), pol-luc (columns 2, 5 and 8) and pp28-luc (columns 3, 6 and 9) without infection (columns 1–3), upon HCMV infection (columns 4–6) and upon HSV-1 infection (columns 7–9).

The pattern of gene expression by different herpesviruses is similar, and the immediate early viral proteins appear to have related functions. Therefore, we were interested in finding out if the reporter system described above was specific for HCMV. We chose to compare the homologous cytomegalovirus with herpes simplex virus type 1 (HSV-1). The MIEP-luc, pol-luc and pp28-luc reporter cell lines were infected with HCMV (Towne strain) or HSV-1 (both purchased from ATCC) 3 pfu/cell and luciferase activity was quantified 48 hours postinfection. As shown in FIGS. 10 and 11, HCMV infection resulted in significant expression of luciferase while HSV infection only had a slight effect on expression of the reporter gene in each of these cell lines. Western blot analysis revealed that the HSV-1 gC protein, a late viral gene product, was efficiently expressed in HSV-1 infected U373 MG cells (data not shown). Therefore, while HSV-1 infects U373 MG cells and leads to expression of late phase genes, it does not efficiently induce the HCMV MIEP, pol or pp28 promoters, suggesting that activation of these promoters is virus specific. These results indicate that these cell lines may be used to specifically diagnose HCMV infection in a given sample.

Example 4

Screen for Inhibitors of CMV Gene Expression

This Example illustrates the use of the cell lines of Example 1 for identifying inhibitors of viral gene expression.

Cells are maintained in DMEM (Mediatech, Herndon, Va.) supplemented with 10% fetal bovine serum (Gemini Bioproducts, Inc., Calabasas, Calif.), 1% antimycotic/antibiotic (GIBCO, Baltimore, Md.) and 0.6 µg/mL G148 (GIBCO, Baltimore, Md.). Cells are seeded at $3 \times 10^4$ cells per well in flat-bottom, tissue culture treated 96-well plates (Corning, Corning, N.Y.) and incubated for about 18 hours in a 37° C. humidified environment. Appropriately diluted candidate modulators are then added directly to the media on cells to a final concentration of 10 µg/mL, and the plates incubated for 30 minutes at 37° C. HCMV (Towne strain, ATCC) is then added at 3 pfu/cell. Forty-eight hours post-infection, the cells are washed once with PBS (without $Ca^{++}$ and $Mg^{++}$) and lysed in the 96-well plate. An aliquot of the cell lysate is then transferred to a black 96-well plate (Packard, Hartford, Conn.) and luciferase assay reagent (Promega, Madison, Wis.) is added to the plate. Luciferase activity (luminescence) in each well is then measured using a Packard Topcount™.

Candidate compounds that result in luciferase activity that is approximately one-fold above the average mean signal obtained from cells incubated in the presence of virus, but in the absence of modulator are selected for further study as inducers of CMV gene expression. Candidate compounds generating a signal that is approximately 25%, preferably greater than 50% below the mean in the absence of modulator are inhibitors of CMV gene expression and have therapeutic potential as antiviral agents.

Example 5

Activity of Representative Anti-Viral Agents

This Example illustrates anti-viral activity of representative compounds of this invention as determined in accordance with Examples 1–4 above.

Figure 12A:
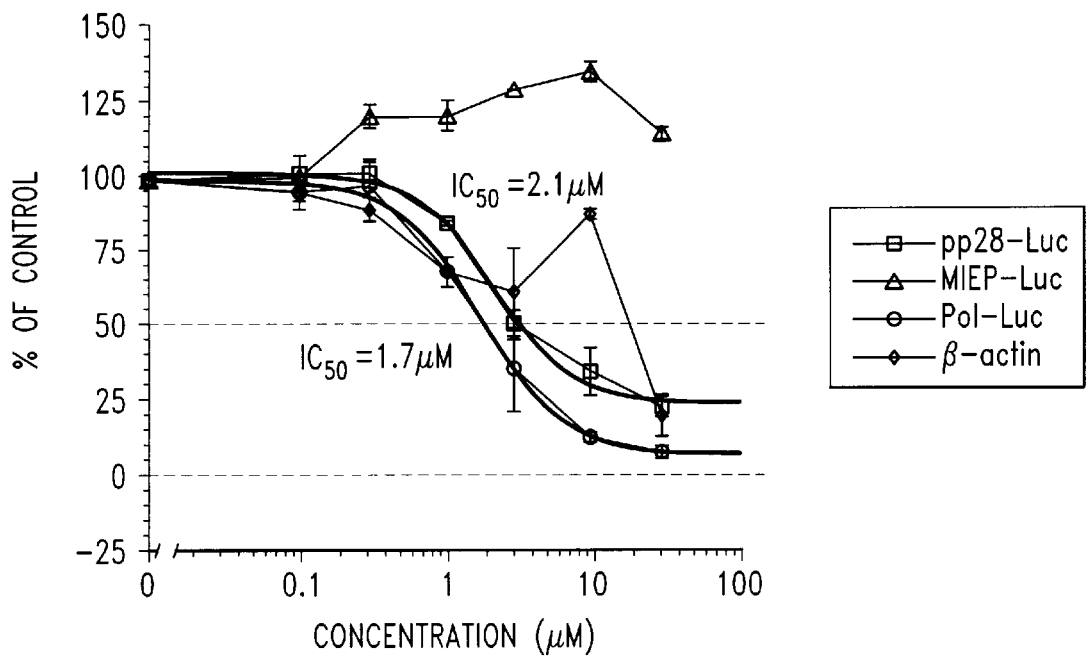
FIGS. 12A and 12B are graphs illustrating luciferase activity detected in MIEP-luc, pol-luc, pp28-luc and β-actin-luc cells 48 hours after infection with 3 pfu/cell of HCMV in presence of vehicle alone or vehicle with increasing amounts of representative anti-viral agents of this invention.
Figure 12B:
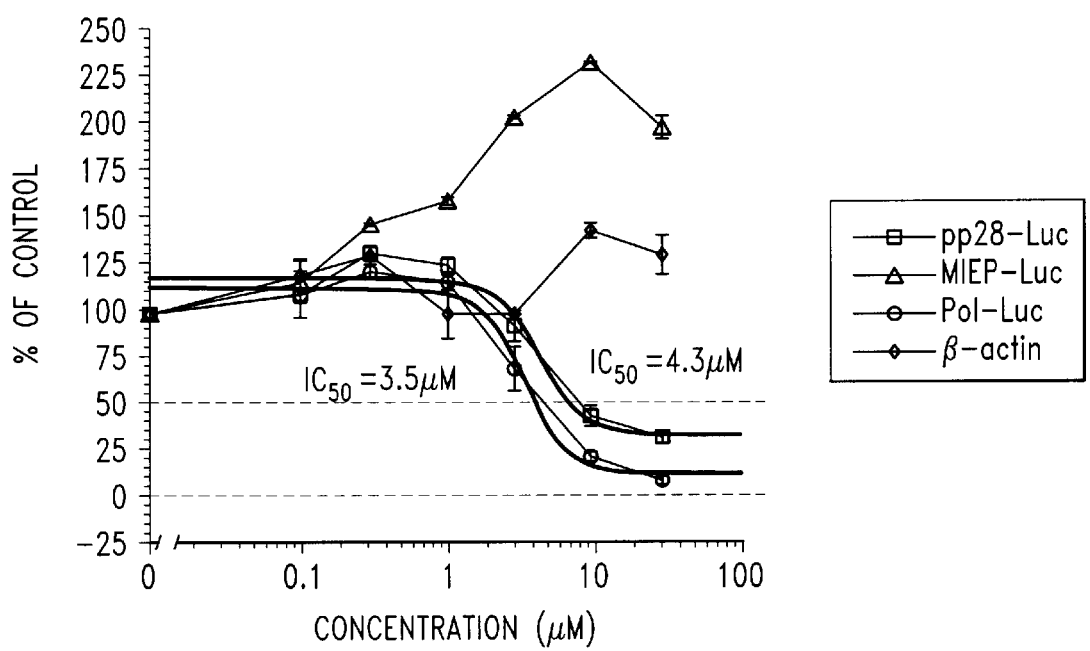

In particular, compounds of structures (IV) and (V) (Aldrich Chem. Co., Milwaukee, Wis.) were assayed for luciferase activity in MIEP-luc, pol-luc, pp28-luc and β-actin-luc cells 48 hours after infection with 3 pfu/cell of HCMV in presence of vehicle (DMSO) alone or vehicle with increasing amounts of the test compounds. The results of these assays are presented in FIGS. 12A and 12B for compounds of structure (IV) and (V), respectively. These results show the specific inhibition of luciferase reporter when expressed from the HCMV pol or pp28 promoters, while no inhibition is detected of reporter gene expressed from the MIEP viral immediate early or β-actin cellular promoters. This represents the anticipated pattern for IE86 inhibitor compounds.

Example 6

Further Activity of Representative Anti-Viral Agents

This Example illustrates further anti-viral activity of representative compounds of this invention.

Infectious Virus Yield Assay for HCMV

Figure 13A:
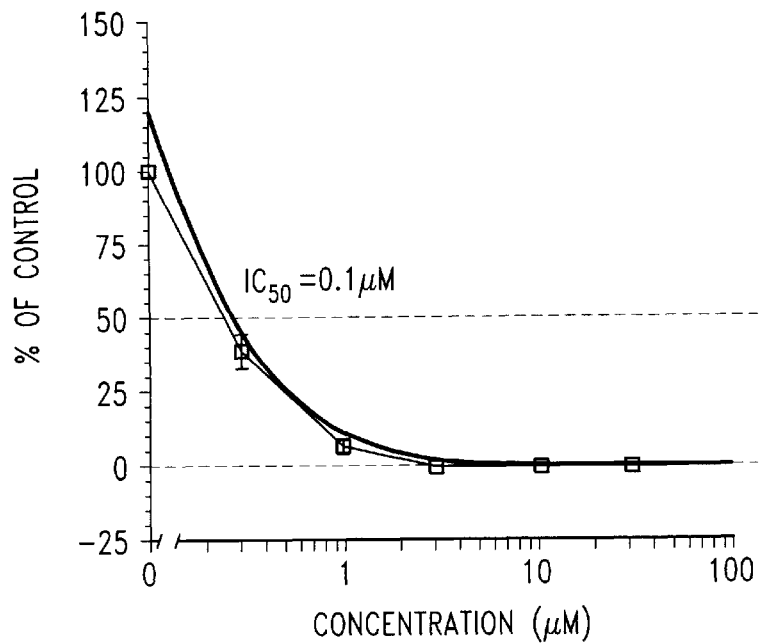
FIGS. 13A and 13B are graphs illustrating the activity of representative anti-viral agents of this invention on production of infectious virus evaluated in yield reduction assays where U373 MG cells were infected with HCMV Towne strain (ATCC), with viral titers determined by plaque assay using human foreskin fibroblast cell monolayers.
Figure 13B:
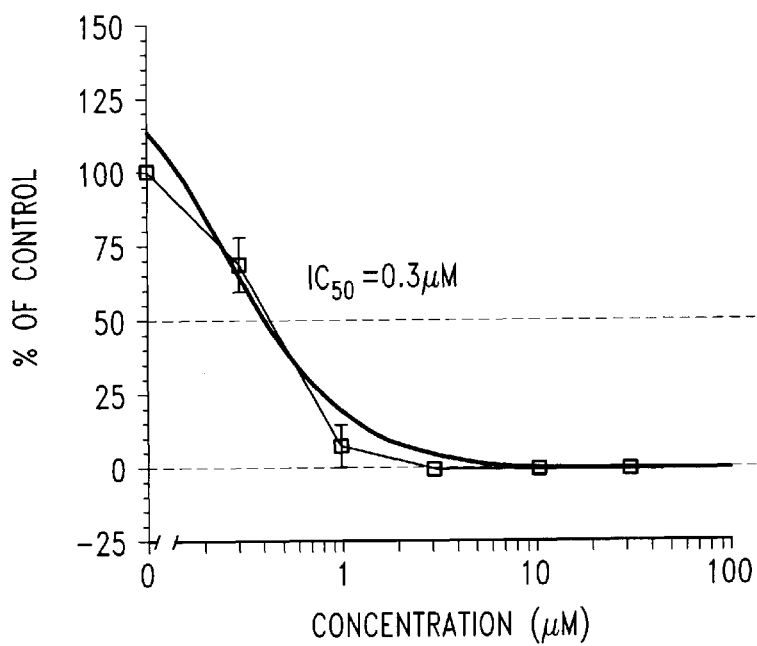

The effect of each test compound on the production of infectious virus was assessed in yield reduction assays where U373 MG cells were infected with HCMV Towne strain (ATCC) at 1 pfu/cell in the absence or presence of increasing amounts of test compound for 5–7 days. Viral titers were determined in duplicate by plaque assay using human foreskin fibroblast cell monolayers. The 50 percent inhibitory concentrations, $IC_{50}$, are shown in FIG. 13A for compound (IV) and FIG. 13B for compound (V).

Infectious Virus Yield Assay for MCMV

Figure 14A:
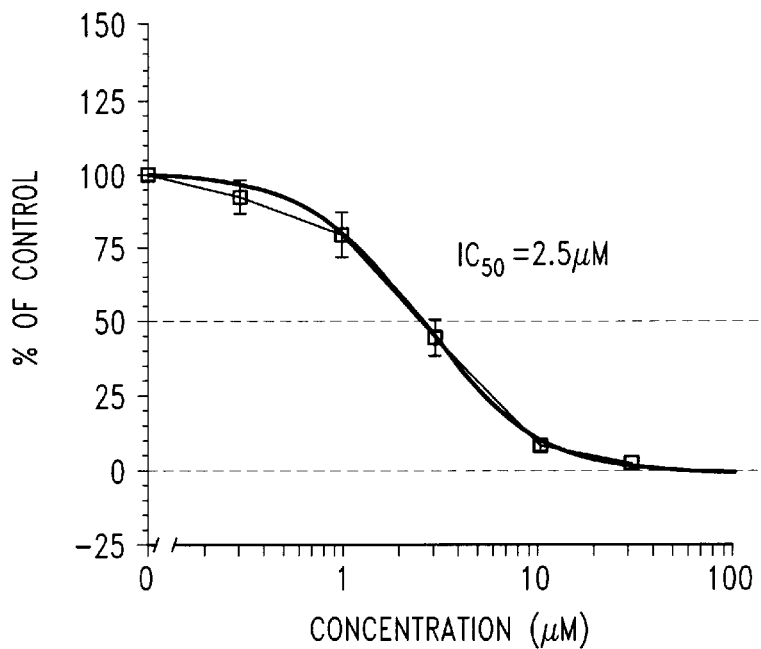
FIGS. 14A and 14B are graphs illustrating the activity of representative anti-viral agents of this invention on production of infectious virus evaluated in yield reduction assays where NIH 3T3 cells were infected with MCMV (ATCC), with viral titers determined by plaque assay using NIH 3T3 cells.
Figure 14B:
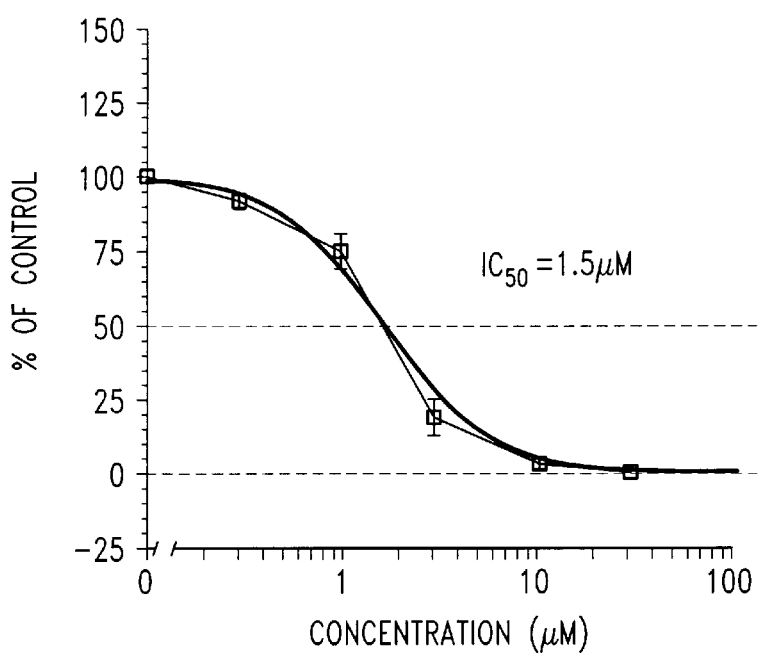

The effect of each test compound on the production of infectious virus was assessed in yield reduction assays where NIH 3T3 cells were infected with MCMV (ATCC) at 1 pfu/cell in the absence or presence of increasing amounts of test compound for 5–7 days. Viral titers were determined in duplicate by plaque assay using NIH 3T3 cells. The 50 percent inhibitory concentrations, $IC_{50}$, are shown in FIG. 14A for compound (IV) and FIG. 14B for compound (V).

Infectious Virus Yield Assay for HSV

Figure 15A:
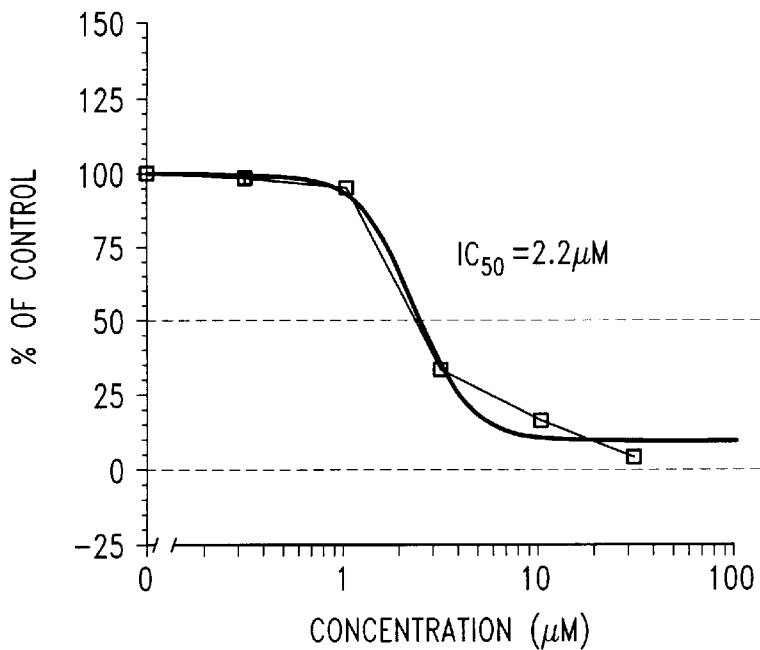
FIGS. 15A and 15B are graphs illustrating the activity of representative anti-viral agents of this invention on production of infectious virus evaluated in yield reduction assays where Vero cells were infected with HSV-1 (ATCC), with viral titers determined by plaque assay in human foreskin fibroblast cell monolayers.
Figure 15B:
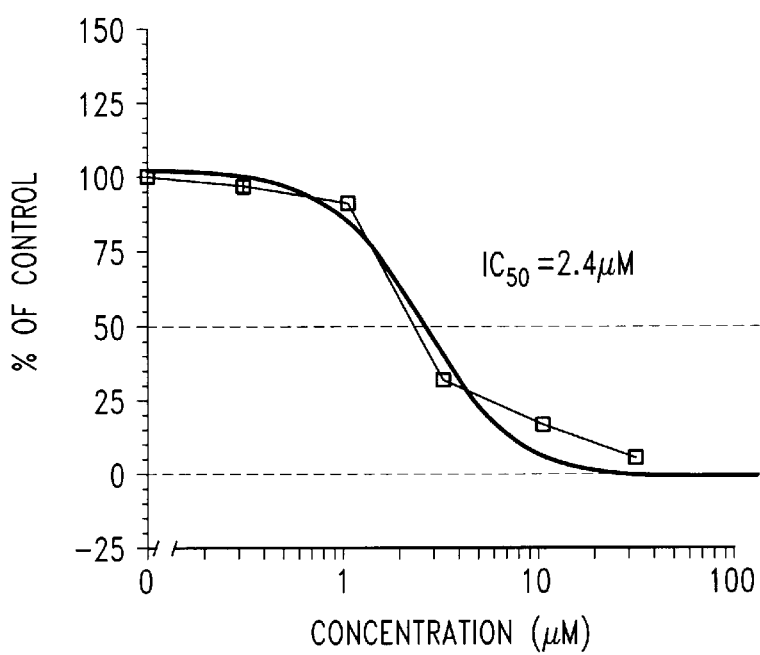

The effect of each test compound on the production of infectious virus was assessed in yield reduction assays where Vero cells were infected with HSV-1 (ATCC) at 1 pfu/cell in the absence or presence of increasing amounts of test compound for 2–3 days. Viral titers were determined in duplicate by plaque assay in Vero cell monolayers. The 50 percent inhibitory concentrations, $IC_{50}$, are shown in FIG. 15A and FIG. 15B for compound (IV) and compound (V), respectively.

Cytotoxic Effects of Anti-Viral Compounds

Figure 16A:
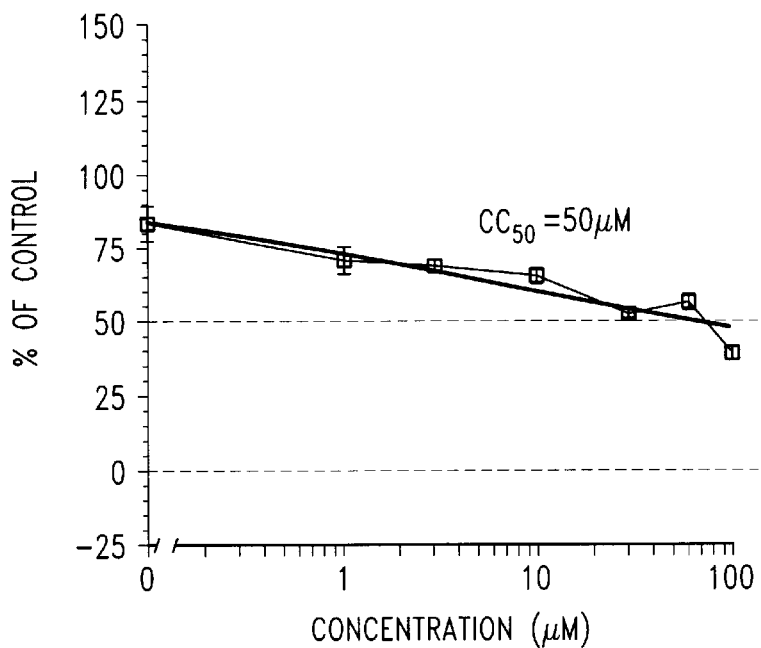
FIGS. 16A and 16B are graphs illustrating the activity of representative anti-viral agents of this invention on cell proliferation and viability.
Figure 16B:
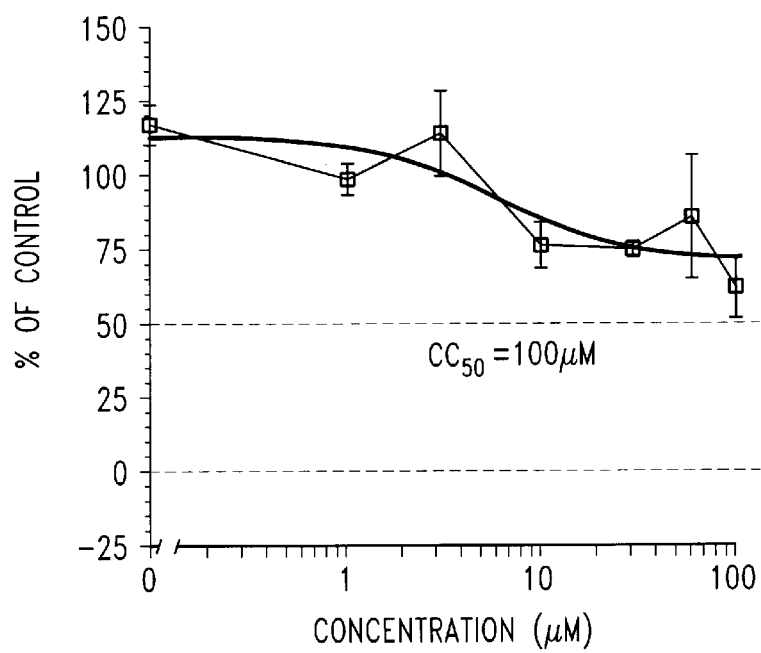

The effect of test compounds on cell proliferation and viability were determined. U373 MG cells were seeded at 3×10⁴ cells per well in a volume of 0.2 ml into 96-well plates and allowed to proliferate for 24 hours in growth medium. Twenty-four hours later, fresh media containing different concentrations of test compounds was added to duplicate wells. After incubating for three days at 37° C., 5% CO2, cells were trypsinized and counted. The 50 percent cytotoxic concentration, $CC_{50}$, relative to untreated cells is shown in FIGS. 16A and 16B for compound (IV) and compound (V), respectively.

Figure 17:
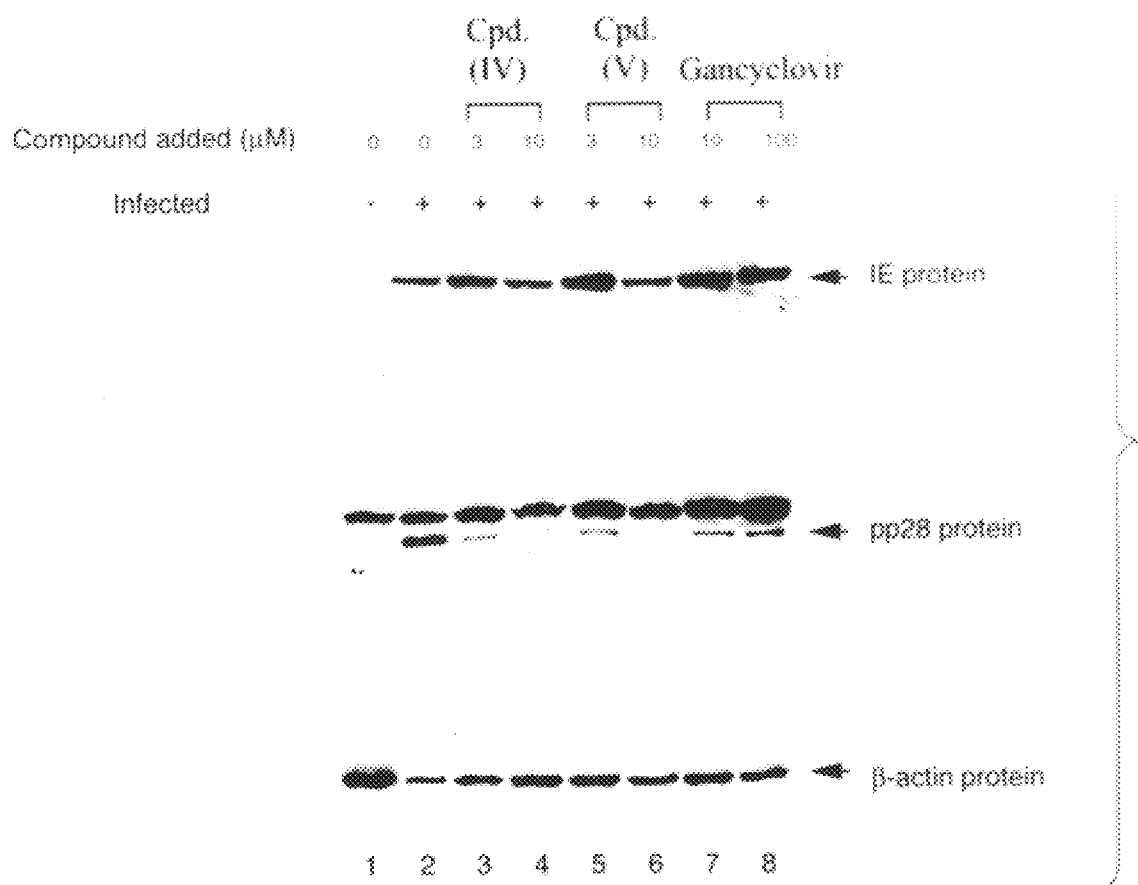
FIG. 17 illustrates the effect of representative anti-viral agents of this invention on expression of HCMV immediate early and late protein expression employing Gancyclovir as a comparative control.

Effect of Anti-Viral Compounds on Expression of HCMV Immediate Early and Late Protein Expression HCMV at 1 pfu/cell were allowed to adsorb to U373 MG cells for 2 hours. Cells were left untreated or were treated with the indicated concentrations of compound (IV), compound (V) or Gancyclovir. Cells were harvested at 72 hours after addition of compound, lysates prepared and separated by SDS-PAGE. The expression of IE, pp28 and the cellular β-actin protein, indicated by arrows in FIG. 17, were detected by western blot.

Effect of Anti-viral Compounds on Viral mRNA Expression

Figure 18:
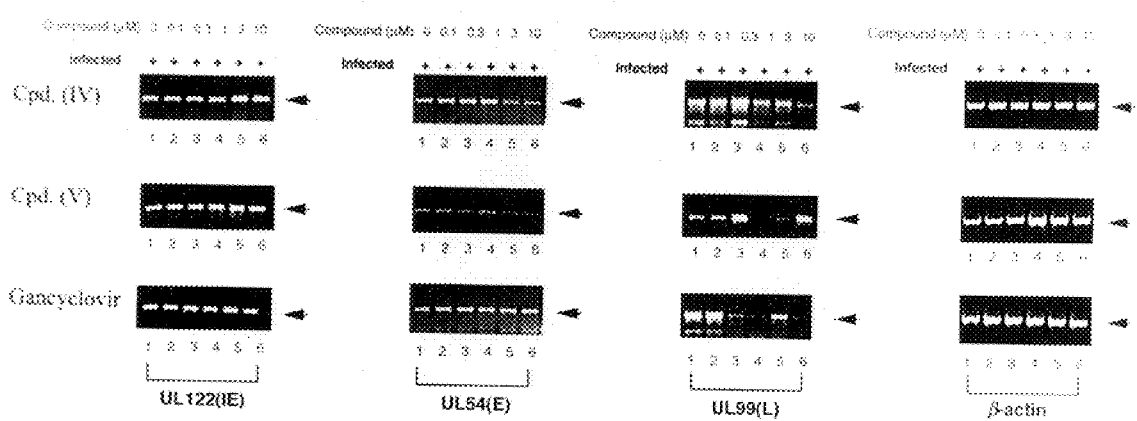
FIG. 18 illustrates the effect of representative anti-viral agents of this invention on viral mRNA expression, again using Gancyclovir as a comparative control.

HCMV at 1 pfu/cell were allowed to adsorb to U373 MG cells for 2 hours. Cells were left untreated or were treated with the indicated concentrations of compound (IV), compound (V) or Gancyclovir. Cells were harvested at 72 hours after addition of compound and total RNA extracted. UL122 (IE), UL54 (E), UL99 (L) and β-actin mRNA expression was determined by RT-PCR, the results of which are presented in FIG. 18.

From the foregoing, it will be evident that although specific embodiments of the invention have been described herein for the purpose of illustration, various modifications may be made without deviating from the spirit or scope of the invention.

What is claimed is:

1. A method for inhibiting replication of viruses of the herpes virus family in an animal, comprising administering to the animal an effective amount of a compound having the structure:

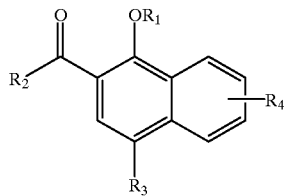

including pharmaceutically acceptable salts thereof, wherein
$R_1$ is hydrogen;
$R_2$ is hydroxy, —$OCOR_5$; —$OR_6$; —$NHR_7$ or —$N(R_7)(R_8)$;
$R_3$ is hydrogen or halogen;
$R_4$ represents from zero to four substituents, wherein each substituent is independently halogen, hydroxy, amino, —$OR_5$ or —$R_6$;
$R_5$ is an unsubstituted or substituted $C_{1-8}$alkyl moiety;
$R_6$ is an unsubstituted or substituted $C_{1-8}$alkyl moiety, an unsubstituted or substituted $C_{6-12}$aryl moiety, or an unsubstituted or substituted $C_{7-12}$aralkyl moiety; and
$R_7$ and $R_8$ are independently an unsubstituted or substituted $C_{6-12}$aryl moiety, or an unsubstituted or substituted $C_{7-12}$aralkyl moiety.

2. The method of claim 1 wherein the virus is cytomegalovirus, herpes simplex virus, human herpes virus, herpes varicella-zoster virus, Epstein-Barr virus or human lymphotrophic virus.

3. The method of claim 1 wherein the virus is cytomegalovirus.

4. The method of claim 1 wherein the virus is herpes simplex virus or human herpes virus.

5. The method of claim 1 wherein $R_2$ is —NH $R_7$.

6. The method of claim 5 wherein $R_7$ is an unsubstituted or substituted $C_{6-12}$aryl moiety.

7. The method of claim 6 wherein $R_7$ is a substituted benzyl moiety.

8. The method of claim 1 wherein $R_3$ is chloro.

9. The method of claim 1 wherein $R_4$ represents zero substituents.

10. The method of claim 1 wherein $R_2$ is a —$NHR_7$ where $R_7$ is a substituted phenyl moiety, $R_3$ is halogen and $R_4$ represents zero substituents.

11. The method of claim 10 wherein $R_3$ is chloro.

12. A method for inhibiting replication of viruses of the herpes virus family in an animal, comprising administering to the animal an effective amount of a compound having the structure:

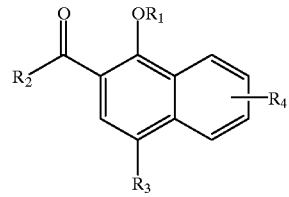

including pharmaceutically acceptable salts thereof, wherein
$R_1$ is hydrogen, —$COR_5$ or —$R_6$;
$R_2$ is hydroxy, —$OCOR_5$; —$OR_6$; —$NHR_7$ or —$N(R_7)(R_8)$;
$R_3$ is halogen;
$R_4$ represents from one to four substituents, wherein each substituent is independently halogen, hydroxy, amino, —$OR_5$ or —$R_6$;
$R_5$ is an unsubstituted or substituted $C_{1-8}$alkyl moiety;
$R_6$ is an unsubstituted or substituted $C_{1-8}$alkyl moiety, an unsubstituted or substituted $C_{6-12}$aryl moiety, or an unsubstituted or substituted $C_{7-12}$aralkyl moiety; and
$R_7$ and $R_8$ are independently an unsubstituted or substituted $C_{6-12}$aryl moiety, or an unsubstituted or substituted $C_{7-12}$aralkyl moiety.

13. The method of claim 12 wherein the virus is cytomegalovirus, herpes simplex virus, human herpes virus, herpes varicella-zoster virus, Epstein-Barr virus or human lymphotrophic virus.

14. The method of claim 12 wherein the virus is cytomegalovirus.

15. The method of claim 12 wherein the virus is herpes simplex virus or human herpes virus.

16. The method of claim 12 wherein $R_1$ is hydrogen.

17. The method of claim 12 wherein $R_2$ is —NH $R_7$.

18. The method of claim 17 wherein $R_7$ is an unsubstituted or substituted $C_{6-12}$aryl moiety.

19. The method of claim 18 wherein $R_7$ is a substituted benzyl moiety.

20. The method of claim 12 wherein $R_3$ is chloro.

21. The method of claim 12 wherein $R_4$ represents zero substituents.

22. The method of claim 12 wherein $R_1$ is hydrogen, $R_2$ is a —$NHR_7$ where $R_7$ is a substituted phenyl moiety, and $R_4$ represents zero substituents.

23. The method of claim 22 wherein $R_3$ is chloro.

* * * * *